United States Patent [19]
Su et al.

[11] Patent Number: 6,162,613
[45] Date of Patent: Dec. 19, 2000

[54] METHODS FOR DESIGNING INHIBITORS OF SERINE/THREONINE-KINASES AND TYROSINE KINASES

[75] Inventors: Michael Shin-San Su, Newton; Ted Fox, Maynard; Keith Philip Wilson, Brookline; Ursula A. Germann, Newton, all of Mass.

[73] Assignee: Vertex Pharmaceuticals, Inc., Cambridge, Mass.

[21] Appl. No.: 09/025,580

[22] Filed: Feb. 18, 1998

[51] Int. Cl.[7] .............................. C12Q 1/48; G06F 19/00
[52] U.S. Cl. .................. 435/15; 435/194; 702/19
[58] Field of Search ....................... 435/15, 194; 702/19

[56] References Cited

FOREIGN PATENT DOCUMENTS

WO 93/02209  2/1993  WIPO .
WO 98/35048  8/1998  WIPO .

OTHER PUBLICATIONS

Singh et al., "Structure–Based Design of a Potent, Selective, and Irreversible Inhibitor of the Catalytic Domain of the erbB Receptor Subfamily of Protein Tyrosine Kinases," *J. Med. Chem.* 40, 1130–1135 (1997).

Wilson et al., "The Structural Basis for the Specificity of Pyridinylimidazole Inhibitors of p38 MAP Kinase," *Chem. & Biol.* 4, 423–431 (1997).

Gum et al., "Acquisition of Sensitivity of Stress–Activated Protein Kinases to the p38 Inhibitor, SB 203580, by Alteration of One or More Amino acids within the ATP Binding Pocket," *J. Biol. Chem.* 273, 15605–15610 (1998).

Goldsmith et al., "Protein Kinases," *Curr. Opin. Struct. Biol.* 4, 833–840 (1994).

Johnson et al., "Active and Inactive Protein Kinases: Structural Basis for Regulation," *Cell* 85, 149–158 (1996).

Taylor et al., "Three Protein Kinase Structures Define a Common Motif," *Structure* 2, 345–355 (1994).

Fox et al. "A single amino acid substitution makes ERK2 susceptible to pyridinyl imidazol inhibitors of p38 MAP kinase" Protein Scince 7, 2249–2255, Nov. 1998.

*Primary Examiner*—Nashaat T. Nashed
*Attorney, Agent, or Firm*—Fish & Neave; James F. Haley; Karen E. Brown

[57] ABSTRACT

The invention relates to methods for designing inhibitors of serine/threonine kinases and tyrosine kinases, particularly MAP kinases, through the use of ATP-binding site mutants of those kinases. The methods of this invention take advantage of the fact that the mutant kinases are capable of binding inhibitory compounds of other kinases with greater affinity than the corresponding wild-type kinase. The invention further relates to the mutant kinases themselves and crystallizable co-complexes of the mutant kinase and the inhibitory compound.

9 Claims, No Drawings

6,162,613

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
        (A) LENGTH: 360 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

```
Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
            35                  40                  45

Arg Val Ala Val Lys Lys Leu Ser Arg Pro Phe Gln Ser Ile Ile His
    50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
            115                 120                 125

Phe Leu Ile Tyr Gln Ile Leu Arg Gly Leu Lys Tyr Ile His Ser Ala
    130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
    195                 200                 205

Val Gly Cys Ile Met Ala Glu Leu Leu Thr Gly Arg Thr Leu Phe Pro
210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
    275                 280                 285

Leu Val Leu Asp Ser Asp Lys Arg Ile Thr Ala Ala Gln Ala Leu Ala
290                 295                 300
```

-continued

```
His Ala Tyr Phe Ala Gln Tyr His Asp Pro Asp Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
                340                 345                 350

Leu Asp Gln Glu Glu Met Glu Ser
            355                 360
```

(2) INFORMATION FOR SEQ ID NO:2:

(i) SEQUENCE CHARACTERISTICS:
        (A) LENGTH: 360 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Region
        (B) LOCATION: 103..104
        (D) OTHER INFORMATION: /note= "amino acid 103 is
            isoleucine or leucine"

(ix) FEATURE:
        (A) NAME/KEY: Region
        (B) LOCATION: 105..106
        (D) OTHER INFORMATION: /product= "OTHER"
            /note= "amino acid 105 is glutamine, threonine or
            alanine"

(ix) FEATURE:
        (A) NAME/KEY: Region
        (B) LOCATION: 106..107
        (D) OTHER INFORMATION: /product= "OTHER"
            /note= "amino acid 106 is aspartic acid or histidine"

(ix) FEATURE:
        (A) NAME/KEY: Region
        (B) LOCATION: 109..110
        (D) OTHER INFORMATION: /product= "OTHER"
            /note= "amino acid 109 is glutamic acid or glycine"

(ix) FEATURE:
        (A) NAME/KEY: Region
        (B) LOCATION: 110..111
        (D) OTHER INFORMATION: /product= "OTHER"
            /note= "amino acid 110 is threonine or alanine"

(xi) SEQUENCE DESCRIPTION: SEQ ID NO:2:

```
Met Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
                20                  25                  30

Glu Gly Ala Tyr Gly Met Val Cys Ser Ala Tyr Asp Asn Val Asn Lys
                35                  40                  45

Val Arg Val Ala Ile Lys Lys Ile Ser Pro Phe Glu His Gln Thr Tyr
50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Xaa Val Xaa Xaa Leu Met Xaa Xaa Asp Leu
                100                 105                 110

Tyr Lys Leu Leu Lys Thr Gln His Leu Ser Asn Asp His Ile Cys Tyr
                115                 120                 125
```

```
Phe Leu Tyr Gln Ile Leu Arg Gly Leu Lys Tyr Ile His Ser Ala Asn
    130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Thr Glu Tyr Val Ala Thr Arg Trp
            180                 185                 190

Tyr Arg Ala Pro Glu Ile Met Leu Asn Ser Lys Gly Tyr Thr Lys Ser
        195                 200                 205

Ile Asp Ile Trp Ser Val Gly Cys Ile Leu Ala Glu Met Leu Ser Asn
    210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
                245                 250                 255

Asn Leu Lys Ala Arg Asn Tyr Leu Leu Ser Leu Pro His Lys Asn Lys
            260                 265                 270

Val Pro Trp Asn Arg Leu Phe Pro Asn Ala Asp Ser Lys Ala Leu Asp
        275                 280                 285

Leu Leu Asp Lys Met Leu Thr Phe Asn Pro His Lys Arg Ile Glu Val
    290                 295                 300

Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
                325                 330                 335

Asp Leu Pro Lys Glu Lys Leu Lys Glu Leu Ile Phe Glu Glu Thr Ala
            340                 345                 350

Arg Phe Gln Pro Gly Tyr Arg Ser
        355                 360

(2) INFORMATION FOR SEQ ID NO:3:

(i) SEQUENCE CHARACTERISTICS:
        (A) LENGTH: 422 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Region
        (B) LOCATION: 146..147
        (D) OTHER INFORMATION: /product= "OTHER"
            /note= "amino acid 146 is methionine, threonine or
            alanine"

(ix) FEATURE:
        (A) NAME/KEY: Region
        (B) LOCATION: 150..151
        (D) OTHER INFORMATION: /product= "OTHER"
            /note= "amino acid 150 is aspartic acid or glycine"

(xi) SEQUENCE DESCRIPTION: SEQ ID NO:3:

Met Ser Leu His Phe Leu Tyr Tyr Cys Ser Glu Pro Thr Leu Asp Val
1               5                   10                  15

Lys Ile Ala Phe Cys Gln Gly Asp Lys Gln Val Asp Val Ser Tyr
            20                  25                  30

Ile Ala Lys His Tyr Asn Met Ser Lys Ser Lys Val Asp Asn Gln Phe
```

```
                35                  40                  45
Tyr Ser Val Glu Val Gly Asp Ser Thr Phe Thr Val Leu Lys Arg Tyr
 50                  55                  60

Gln Asn Leu Lys Pro Ile Gly Ser Gly Ala Gln Gly Ile Val Cys Ala
 65                  70                  75                  80

Ala Tyr Asp Ala Val Leu Asp Arg Asn Val Ala Ile Lys Lys Leu Ser
                 85                  90                  95

Arg Pro Phe Gln Asn Gln Thr His Ala Lys Arg Ala Tyr Arg Glu Leu
                100                 105                 110

Val Leu Met Lys Cys Val Asn His Lys Asn Ile Ile Ser Leu Leu Asn
            115                 120                 125

Val Phe Thr Pro Gln Lys Thr Leu Glu Glu Phe Gln Asp Val Tyr Leu
        130                 135                 140

Val Xaa Glu Leu Met Xaa Ala Asn Leu Cys Gln Val Ile Gln Met Glu
145                 150                 155                 160

Leu Asp His Glu Arg Met Ser Tyr Leu Leu Tyr Gln Met Leu Cys Gly
                165                 170                 175

Ile Lys His Leu His Ser Ala Gly Ile Ile His Arg Asp Leu Lys Pro
            180                 185                 190

Ser Asn Ile Val Val Lys Ser Asp Cys Thr Leu Lys Ile Leu Asp Phe
        195                 200                 205

Gly Leu Ala Arg Thr Ala Gly Thr Ser Phe Met Met Thr Pro Tyr Val
    210                 215                 220

Val Thr Arg Tyr Tyr Arg Ala Pro Glu Val Ile Leu Gly Met Gly Tyr
225                 230                 235                 240

Lys Glu Asn Val Asp Ile Trp Ser Val Gly Cys Ile Met Gly Glu Met
                245                 250                 255

Val Arg His Lys Ile Leu Phe Pro Gly Arg Asp Tyr Ile Asp Gln Trp
            260                 265                 270

Asn Lys Val Ile Glu Gln Leu Gly Thr Pro Cys Pro Glu Phe Met Lys
        275                 280                 285

Lys Leu Gln Pro Thr Val Arg Asn Tyr Val Glu Asn Arg Pro Lys Tyr
    290                 295                 300

Ala Gly Leu Thr Phe Pro Lys Leu Phe Pro Asp Ser Leu Phe Pro Ala
305                 310                 315                 320

Asp Ser Glu His Asn Lys Leu Lys Ala Ser Gln Ala Arg Asp Leu Leu
                325                 330                 335

Ser Lys Met Leu Val Ile Asp Pro Ala Lys Arg Ile Ser Val Asp Asp
            340                 345                 350

Ala Leu Gln His Pro Tyr Ile Asn Val Trp Tyr Asp Pro Ala Glu Val
        355                 360                 365

Glu Ala Pro Pro Pro Gln Ile Tyr Asp Lys Gln Leu Asp Glu Arg Glu
    370                 375                 380

His Thr Ile Glu Glu Trp Lys Glu Leu Ile Tyr Lys Glu Val Met Asn
385                 390                 395                 400

Ser Glu Glu Lys Thr Lys Asn Gly Val Val Lys Gly Gln Pro Ser Pro
                405                 410                 415

Ser Ala Gln Val Gln Gln
                420
```

(2) INFORMATION FOR SEQ ID NO:4:

(i) SEQUENCE CHARACTERISTICS:
        (A) LENGTH: 30 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:4:

GAACGGCGGG CAGCCAACAT GGCGGCGGCG                                    30

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:5:

GGGCTCGAGC CTGACAAATT TAAGATCTGT ATCCTG                              36

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:6:

TTAACATATG GCGGCGGCGG CGGCGGCG                                       28

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:7:

CCCACAGGAT CCGATCTGTA TCCTG                                          25

(2) INFORMATION FOR SEQ ID NO:8:

(i) SEQUENCE CHARACTERISTICS:

(A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:8:

GATGGTCCGC GGGCAGGTGT TCG                                                    23

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:9:

GTGTCTTCAA AAGCTTGTAA AGATCTGTTT CC                                          32

(2) INFORMATION FOR SEQ ID NO:10:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:10:

CAAAAGCTTG TAAAGATCTG TTTCCATGAG GTCCGTTACT AT                               42

(2) INFORMATION FOR SEQ ID NO:11:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:11:

CAAAAGCTTG TAAAGATCTG TTTCCATGAG GTCCGCTACT AT                               42

(2) INFORMATION FOR SEQ ID NO:12:

```
    (i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:12:

CAAAAGCTTG TAAAGATCTG CTCCCATGAG GTGCGTTACT AGATATAC                48

(2) INFORMATION FOR SEQ ID NO:13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:13:

GATCTTTACA AGCTTTTGAA GACACAAC                                       28

(2) INFORMATION FOR SEQ ID NO:14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:14:

CTTGGTGTAG CCCTTGGAAT TCAACATA                                       28

(2) INFORMATION FOR SEQ ID NO:15:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: C-terminal (ix) FEATURE:
        (A) NAME/KEY: Region
        (B) LOCATION: 1..6
        (D) OTHER INFORMATION: /note= "C-terminal tag"
```

(xi) SEQUENCE DESCRIPTION: SEQ ID NO:15:

Glu Tyr Met Pro Met Glu
1               5

(2) INFORMATION FOR SEQ ID NO:16:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:16:

CATGGCACAC CATCACCATC ACCATCCCAA GAAGAAGCCG ACGCCCATCC AG          52

(2) INFORMATION FOR SEQ ID NO:17:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:17:

CTGGATGGGC GTCGGCTTCT TCTTGGGATG GTGATGGTGA TGGTGTGC               48

(2) INFORMATION FOR SEQ ID NO:18:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO:18:

GCTCTAGAGC TCCATGGGCA GCAAAAGCAA AGTTGACAA                         39

(2) INFORMATION FOR SEQ ID NO:19:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO

-continued (iv) ANTI-SENSE: NO (xi) SEQUENCE DESCRIPTION: SEQ ID NO:19:

TAGCGGATCC TCATTCTGAA TTCATTACTT CCTTGTA                          37

(2) INFORMATION FOR SEQ ID NO:20:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: NO (xi) SEQUENCE DESCRIPTION: SEQ ID NO:20:

CCAAGATGTT TACTTAGTAG CGGAACTGAT GGATGCCAA                        39

(2) INFORMATION FOR SEQ ID NO:21:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: NO (xi) SEQUENCE DESCRIPTION: SEQ ID NO:21:

CAAGATGTTT ACTTAGTAAC GGGACTGATG GATGCCAAC                         39

(2) INFORMATION FOR SEQ ID NO:22:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iii) HYPOTHETICAL: NO (iv) ANTI-SENSE: NO (xi) SEQUENCE DESCRIPTION: SEQ ID NO:22:

GTAATGGAAC TGATGGGTGC CAACTTATGT CAAGTG                           36

(2) INFORMATION FOR SEQ ID NO:23:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (iii) HYPOTHETICAL: NO

```
          (iv) ANTI-SENSE: NO (ix) FEATURE:
                (A) NAME/KEY: Peptide
                (B) LOCATION: 1..21
                (D) OTHER INFORMATION: /note= "EGF receptor peptide"

(xi) SEQUENCE DESCRIPTION: SEQ ID NO:23:

Lys Arg Glu Leu Val Glu Pro Leu Thr Pro Ser Gly Glu Ala Pro Asn
1               5                   10                  15

Gln Ala Leu Leu Arg
            20

(2) INFORMATION FOR SEQ ID NO:24:

(i) SEQUENCE CHARACTERISTICS:
          (A) LENGTH: 367 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:24:

Met Ser Ser Pro Pro Thr Arg Ser Gly Phe Tyr Arg Gln Glu Val
1               5                   10                  15

Thr Lys Thr Ala Trp Glu Val Arg Ala Val Tyr Arg Asp Leu Gln Pro
            20                  25                  30

Val Gly Ser Gly Ala Tyr Gly Ala Val Cys Ser Ala Val Asp Gly Arg
            35                  40                  45

Thr Gly Ala Lys Val Ala Ile Lys Lys Leu Tyr Arg Pro Phe Gln Ser
        50                  55                  60

Glu Leu Phe Ala Lys Leu Ala Tyr Arg Glu Leu Arg Leu Leu Lys His
65                  70                  75                  80

Met Arg His Glu Asn Val Ile Gly Leu Leu Asp Val Phe Thr Pro Asp
                85                  90                  95

Glu Thr Leu Asp Asp Phe Thr Asp Phe Tyr Leu Val Met Pro Phe Met
                100                 105                 110

Gly Thr Asp Leu Gly Lys Leu Met Lys His Glu Lys Leu Gly Glu Asp
            115                 120                 125

Arg Ile Gln Phe Leu Val Tyr Gln Met Met Lys Gly Leu Arg Tyr Ile
        130                 135                 140

His Ala Ala Gly Ile Ile His Arg Asp Leu Lys Pro Gly Asn Leu Ala
145                 150                 155                 160

Val Asn Glu Asp Cys Glu Leu Lys Ile Leu Asp Phe Gly Leu Ala Arg
                165                 170                 175

Gln Ala Asp Ser Glu Met Thr Gly Tyr Val Val Thr Arg Trp Tyr Arg
            180                 185                 190

Ala Pro Glu Val Ile Leu Asn Trp Ile Ala Tyr Thr Gln Thr Val Asp
            195                 200                 205

Ile Trp Ser Val Gly Cys Ile Met Ala Glu Met Ile Thr Gly Lys Thr
        210                 215                 220

Leu Phe Lys Gly Ser Asp His Leu Asp Gln Leu Lys Glu Ile Met Lys
225                 230                 235                 240

Val Thr Gly Thr Pro Pro Ala Glu Phe Val Gln Arg Leu Gln Ser Asp
                245                 250                 255

Glu Ala Lys Asn Tyr Met Lys Gly Leu Pro Glu Leu Glu Lys Lys Asp
                260                 265                 270
```

```
Phe Ala Ser Ile Leu Thr Asn Ala Ser Pro Leu Ala Val Asn Leu Leu
                275                 280                 285

Glu Lys Met Leu Val Leu Asp Ala Asp Ile Arg Leu Thr Ala Gly Glu
    290                 295                 300

Phe Leu Ser His Pro Tyr Phe Glu Ser Leu His Asp Thr Glu Asp Glu
305                 310                 315                 320

Pro Gln Val Gln Lys Tyr Asp Asp Ser Phe Asp Tyr Phe Asp Arg Thr
                325                 330                 335

Leu Asp Glu Trp Lys Arg Val Thr Tyr Lys Glu Val Leu Ser Phe Lys
                340                 345                 350

Pro Pro Arg Gln Leu Gly Ala Arg Val Ser Lys Glu Thr Pro Leu
                355                 360                 365
```

(2) INFORMATION FOR SEQ ID NO:25:

(i) SEQUENCE CHARACTERISTICS:
        (A) LENGTH: 379 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:25:

```
Met Ala Ala Ala Ala Gln Gly Gly Gly Gly Glu Pro Arg Arg
1               5                   10                  15

Thr Glu Gly Val Gly Pro Gly Val Pro Gly Val Glu Met Val Lys
                20                  25                  30

Gly Gln Pro Phe Asp Val Gly Pro Arg Tyr Thr Gln Leu Gln Tyr Ile
                35                  40                  45

Gly Glu Gly Ala Tyr Gly Met Val Ser Ser Ala Tyr Asp His Val Arg
    50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
                100                 105                 110

Glu Ala Met Arg Asp Val Tyr Ile Val Gln Asp Leu Met Glu Thr Asp
            115                 120                 125

Leu Tyr Lys Leu Leu Lys Ser Gln Gln Leu Ser Asn Asp His Ile Cys
            130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ser Asn Thr
                165                 170                 175

Thr Cys Asp Leu Lys Ile Cys Asp Phe Gly Leu Ala Arg Ile Ala Asp
                180                 185                 190

Pro Glu His Asp His Thr Gly Phe Leu Thr Glu Tyr Val Ala Thr Arg
            195                 200                 205

Trp Tyr Arg Ala Pro Glu Ile Met Leu Asn Ser Lys Gly Tyr Thr Lys
210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255
```

-continued

```
Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
        290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Pro Val Ala Glu Pro Phe Thr Phe Ala Met Glu Leu
                340                 345                 350

Asp Asp Leu Pro Lys Glu Arg Leu Lys Glu Leu Ile Phe Gln Glu Thr
        355                 360                 365

Ala Arg Phe Gln Pro Gly Val Leu Glu Ala Pro
        370                 375
```

(2) INFORMATION FOR SEQ ID NO:26:

(i) SEQUENCE CHARACTERISTICS:
(A) LENGTH: 365 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:26:

```
Met Ser Leu Ile Arg Lys Lys Gly Phe Tyr Lys Gln Glu Leu Asn Lys
1               5                   10                  15

Thr Ala Trp Glu Leu Pro Lys Thr Tyr Val Ser Pro Thr His Val Gly
            20                  25                  30

Ser Gly Ala Tyr Gly Ser Trp Cys Ser Ala Ile Asp Lys Arg Ser Gly
        35                  40                  45

Glu Lys Val Ala Ile Lys Lys Leu Ser Arg Pro Phe Gln Ser Glu Ile
    50                  55                  60

Phe Ala Lys Arg Ala Tyr Arg Glu Leu Leu Leu Leu Lys His Met Gln
65                  70                  75                  80

His Glu Asn Val Ile Gly Leu Leu Asp Val Phe Thr Pro Ala Ser Ser
                85                  90                  95

Leu Arg Asn Phe Tyr Asp Phe Tyr Leu Val Met Pro Phe Met Gln Thr
            100                 105                 110

Asp Leu Gln Lys Ile Met Gly Met Glu Phe Ser Glu Glu Lys Ile Gln
        115                 120                 125

Tyr Leu Val Tyr Gln Met Leu Lys Gly Leu Lys Tyr Ile His Ser Ala
    130                 135                 140

Gly Val Val His Arg Asp Leu Lys Pro Gly Asn Leu Ala Val Asn Glu
145                 150                 155                 160

Asp Cys Glu Leu Lys Ile Leu Asp Phe Gly Leu Ala Arg His Ala Asp
                165                 170                 175

Ala Glu Met Thr Gly Tyr Val Val Thr Arg Trp Tyr Arg Ala Pro Glu
            180                 185                 190

Val Ile Leu Ser Trp Met His Tyr Asn Gln Thr Val Asp Ile Trp Ser
        195                 200                 205

Val Gly Cys Ile Met Ala Glu Met Leu Thr Gly Lys Thr Leu Phe Lys
    210                 215                 220
```

-continued

```
Gly Lys Asp Tyr Leu Asp Gln Leu Thr Gln Ile Leu Lys Val Thr Gly
225                 230                 235                 240

Val Pro Gly Thr Glu Phe Val Gln Lys Leu Asn Asp Lys Ala Ala Lys
            245                 250                 255

Ser Tyr Ile Gln Ser Leu Pro Gln Thr Pro Arg Lys Asp Phe Thr Gln
            260                 265                 270

Leu Phe Pro Arg Ala Ser Pro Gln Ala Ala Asp Leu Leu Glu Lys Met
        275                 280                 285

Leu Glu Leu Asp Val Asp Lys Arg Leu Thr Ala Gln Ala Leu Thr
    290                 295                 300

His Pro Phe Phe Glu Pro Phe Arg Asp Pro Glu Glu Thr Glu Ala
305                 310                 315                 320

Gln Gln Pro Phe Asp Asp Ser Leu Glu His Glu Lys Leu Thr Val Asp
                325                 330                 335

Glu Trp Lys Gln His Ile Tyr Lys Glu Ile Val Asn Phe Ser Pro Ile
            340                 345                 350

Ala Arg Lys Asp Ser Arg Arg Ser Gly Met Lys Leu
            355                 360                 365
```

(2) INFORMATION FOR SEQ ID NO:27:

(i) SEQUENCE CHARACTERISTICS:
        (A) LENGTH: 365 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:27:

```
Met Ser Leu Ile Arg Lys Lys Gly Phe Tyr Lys Gln Asp Val Asn Lys
1               5                   10                  15

Thr Ala Trp Glu Leu Pro Lys Thr Tyr Val Ser Pro Thr His Val Gly
            20                  25                  30

Ser Gly Ala Tyr Gly Ser Val Cys Ser Ala Ile Asp Lys Arg Ser Gly
        35                  40                  45

Glu Lys Val Ala Ile Lys Lys Leu Ser Arg Pro Phe Gln Ser Glu Ile
50                  55                  60

Phe Ala Lys Arg Ala Tyr Arg Glu Leu Leu Leu Lys His Met Gln
65                  70                  75                  80

His Glu Asn Val Ile Gly Leu Leu Asp Val Phe Thr Pro Ala Ser Ser
                85                  90                  95

Leu Arg Asn Phe Tyr Asp Phe Tyr Leu Val Met Pro Phe Met Gln Thr
            100                 105                 110

Asp Leu Gln Lys Ile Met Gly Met Glu Phe Ser Glu Glu Lys Ile Gln
            115                 120                 125

Tyr Leu Val Tyr Gln Met Leu Lys Gly Leu Lys Tyr Ile His Ser Ala
    130                 135                 140

Gly Val Val His Arg Asp Leu Lys Pro Gly Asn Leu Ala Val Asn Glu
145                 150                 155                 160

Asp Cys Glu Leu Lys Ile Leu Asp Phe Gly Leu Ala Arg His Ala Asp
                165                 170                 175

Ala Glu Met Thr Gly Tyr Val Val Thr Arg Trp Tyr Arg Ala Pro Glu
            180                 185                 190

Val Ile Leu Ser Trp Met His Tyr Asn Gln Thr Val Asp Ile Trp Ser
    195                 200                 205
```

-continued

```
Val Gly Cys Ile Met Ala Glu Met Leu Thr Gly Lys Thr Leu Phe Lys
    210                 215                 220

Gly Lys Asp Tyr Leu Asp Gln Leu Thr Gln Ile Leu Lys Val Thr Gly
225                 230                 235                 240

Val Pro Gly Thr Glu Phe Val Gln Lys Leu Asn Asp Lys Ala Ala Lys
                245                 250                 255

Ser Tyr Ile Gln Ser Leu Pro Gln Thr Pro Arg Lys Asp Phe Thr Gln
                260                 265                 270

Leu Phe Pro Arg Ala Ser Pro Gln Ala Ala Asp Leu Leu Glu Lys Met
            275                 280                 285

Leu Glu Leu Asp Val Asp Lys Arg Leu Thr Ala Ala Gln Ala Leu Thr
    290                 295                 300

His Pro Phe Phe Glu Pro Phe Arg Asp Pro Glu Glu Thr Glu Ala
305                 310                 315                 320

Gln Gln Pro Phe Asp Asp Ser Leu Glu His Glu Lys Leu Thr Val Asp
                325                 330                 335

Glu Trp Lys Gln His Ile Tyr Lys Glu Ile Val Asn Phe Ser Pro Ile
                340                 345                 350

Ala Arg Lys Asp Ser Arg Arg Arg Ser Gly Met Lys Leu
            355                 360                 365

(2) INFORMATION FOR SEQ ID NO:28:

(i) SEQUENCE CHARACTERISTICS:
        (A) LENGTH: 464 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:28:

Met Ser Leu His Phe Leu Tyr Tyr Cys Ser Glu Pro Thr Leu Asp Val
1               5                   10                  15

Lys Ile Ala Phe Cys Gln Gly Phe Asp Lys Gln Val Asp Val Ser Tyr
            20                  25                  30

Ile Ala Lys His Tyr Asn Met Ser Lys Ser Lys Val Asp Asn Gln Phe
            35                  40                  45

Tyr Ser Val Glu Val Gly Asp Ser Thr Phe Thr Val Leu Lys Arg Tyr
50                  55                  60

Gln Asn Leu Lys Pro Ile Gly Ser Gly Ala Gln Gly Ile Val Cys Ala
65                  70                  75                  80

Ala Tyr Asp Ala Val Leu Asp Arg Asn Val Ala Ile Lys Lys Leu Ser
                85                  90                  95

Arg Pro Phe Gln Asn Gln Thr His Ala Lys Arg Ala Tyr Arg Glu Leu
            100                 105                 110

Val Leu Met Lys Cys Val Asn His Lys Asn Ile Ile Ser Leu Leu Asn
        115                 120                 125

Val Phe Thr Pro Gln Lys Thr Leu Glu Glu Phe Gln Asp Val Tyr Leu
    130                 135                 140

Val Met Glu Leu Met Asp Ala Asn Leu Cys Gln Val Ile Gln Met Glu
145                 150                 155                 160

Leu Asp His Glu Arg Met Ser Tyr Leu Leu Tyr Gln Met Leu Cys Gly
                165                 170                 175

Ile Lys His Leu His Ser Ala Gly Ile Ile His Arg Asp Leu Lys Pro
            180                 185                 190
```

```
Ser Asn Ile Val Val Lys Ser Asp Cys Thr Leu Lys Ile Leu Asp Phe
        195                 200                 205

Gly Leu Ala Arg Thr Ala Gly Thr Ser Phe Met Met Thr Pro Tyr Val
210                 215                 220

Val Thr Arg Tyr Tyr Arg Ala Pro Glu Val Ile Leu Gly Met Gly Tyr
225                 230                 235                 240

Lys Glu Asn Val Asp Ile Trp Ser Val Gly Cys Ile Met Gly Glu Met
                245                 250                 255

Val Arg His Lys Ile Leu Phe Pro Gly Arg Asp Tyr Ile Asp Gln Trp
            260                 265                 270

Asn Lys Val Ile Glu Gln Leu Gly Thr Pro Cys Pro Glu Phe Met Lys
        275                 280                 285

Lys Leu Gln Pro Thr Val Arg Asn Tyr Val Glu Asn Arg Pro Lys Tyr
    290                 295                 300

Ala Gly Leu Thr Phe Pro Lys Leu Phe Pro Asp Ser Leu Phe Pro Ala
305                 310                 315                 320

Asp Ser Glu His Asn Lys Leu Lys Ala Ser Gln Ala Arg Asp Leu Leu
                325                 330                 335

Ser Lys Met Leu Val Ile Asp Pro Ala Lys Arg Ile Ser Val Asp Asp
            340                 345                 350

Ala Leu Gln His Pro Tyr Ile Asn Val Trp Tyr Asp Pro Ala Glu Val
        355                 360                 365

Glu Ala Pro Pro Pro Gln Ile Tyr Asp Lys Gln Leu Asp Glu Arg Glu
370                 375                 380

His Thr Ile Glu Glu Trp Lys Glu Leu Ile Tyr Lys Glu Val Met Asn
385                 390                 395                 400

Ser Glu Glu Lys Thr Lys Asn Gly Val Val Lys Gly Gln Pro Ser Pro
                405                 410                 415

Ser Gly Ala Ala Val Asn Ser Ser Glu Ser Leu Pro Pro Ser Ser Ser
            420                 425                 430

Val Asn Asp Ile Ser Ser Met Ser Thr Asp Gln Thr Leu Ala Ser Asp
        435                 440                 445

Thr Asp Ser Ser Leu Glu Ala Ser Ala Gly Pro Leu Gly Cys Cys Arg
450                 455                 460

(2) INFORMATION FOR SEQ ID NO:29:

(i) SEQUENCE CHARACTERISTICS:
        (A) LENGTH: 382 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:29:

Met Ser Asp Ser Lys Cys Asp Ser Gln Phe Tyr Ser Val Gln Val Ala
1               5                   10                  15

Asp Ser Thr Phe Thr Val Leu Lys Arg Tyr Gln Gln Leu Lys Pro Ile
            20                  25                  30

Gly Ser Gly Ala Gln Gly Ile Val Cys Ala Ala Phe Asp Thr Val Leu
        35                  40                  45

Gly Ile Ser Val Ala Val Lys Lys Leu Ser Arg Pro Phe Gln Asn Gln
    50                  55                  60

Thr His Ala Lys Arg Ala Tyr Arg Glu Leu Val Leu Leu Lys Cys Val
65                  70                  75                  80
```

```
Asn His Lys Asn Ile Ile Ser Leu Leu Asn Val Phe Thr Pro Gln Lys
            85                  90                  95

Thr Leu Glu Glu Phe Gln Asp Val Tyr Leu Val Met Glu Leu Met Asp
           100                 105                 110

Ala Asn Leu Cys Gln Val Ile His Met Glu Leu Asp His Glu Arg Met
           115                 120                 125

Ser Tyr Leu Leu Tyr Gln Met Leu Cys Gly Ile Lys His Leu His Ser
130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Cys Thr Asn Phe Met Met Thr Pro Tyr Val Val Thr Arg Tyr Tyr Arg
                180                 185                 190

Ala Pro Glu Val Ile Leu Gly Met Gly Tyr Lys Glu Asn Val Asp Ile
                195                 200                 205

Trp Ser Val Gly Cys Ile Met Gly Glu Leu Val Lys Gly Cys Val Ile
            210                 215                 220

Phe Gln Gly Thr Asp His Ile Asp Gln Trp Asn Lys Val Ile Glu Gln
225                 230                 235                 240

Leu Gly Thr Pro Ser Ala Glu Phe Met Lys Lys Leu Gln Pro Thr Val
                245                 250                 255

Arg Asn Tyr Val Glu Asn Arg Pro Lys Tyr Pro Gly Ile Lys Phe Glu
                260                 265                 270

Glu Leu Phe Pro Asp Trp Ile Phe Pro Ser Glu Ser Glu Arg Asp Lys
                275                 280                 285

Ile Lys Thr Ser Gln Ala Arg Asp Leu Leu Ser Lys Met Leu Val Ile
290                 295                 300

Asp Pro Asp Lys Arg Ile Ser Val Asp Glu Ala Leu Arg His Pro Tyr
305                 310                 315                 320

Ile Thr Val Trp Tyr Asp Pro Ala Glu Ala Glu Ala Pro Pro Pro Gln
                325                 330                 335

Ile Tyr Asp Ala Gln Leu Glu Glu Arg Glu His Ala Ile Glu Glu Trp
                340                 345                 350

Lys Glu Leu Ile Tyr Lys Glu Val Met Asp Trp Glu Glu Arg Ser Lys
                355                 360                 365

Asn Gly Val Val Lys Asp Gln Pro Ser Ala Gln Met Gln Gln
370                 375                 380

(2) INFORMATION FOR SEQ ID NO:30:

(i) SEQUENCE CHARACTERISTICS:
        (A) LENGTH: 382 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

Met Ser Asp Ser Lys Cys Asp Ser Gln Phe Tyr Ser Val Gln Val Ala
1               5                   10                  15

Asp Ser Thr Phe Thr Val Leu Lys Arg Tyr Gln Gln Leu Lys Pro Ile
                20                  25                  30

Gly Ser Gly Ala Gln Gly Ile Val Cys Ala Ala Phe Asp Thr Val Leu
            35                  40                  45
```

```
Gly Ile Ser Val Ala Val Lys Lys Leu Ser Arg Pro Phe Gln Asn Gln
     50                  55                  60

Thr His Ala Lys Arg Ala Tyr Arg Glu Leu Val Leu Leu Lys Cys Val
 65                  70                  75                  80

Asn His Lys Asn Ile Ile Ser Leu Leu Asn Val Phe Thr Pro Gln Lys
                 85                  90                  95

Thr Leu Glu Glu Phe Gln Asp Val Tyr Leu Val Met Glu Leu Met Asp
                100                 105                 110

Ala Asn Leu Cys Gln Val Ile His Met Glu Leu Asp His Glu Arg Met
            115                 120                 125

Ser Tyr Leu Leu Tyr Gln Met Leu Cys Gly Ile Lys His Leu His Ser
    130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Cys Thr Asn Phe Met Met Thr Pro Tyr Val Val Thr Arg Tyr Tyr Arg
                180                 185                 190

Ala Pro Glu Val Ile Leu Gly Met Gly Tyr Lys Glu Asn Val Asp Ile
        195                 200                 205

Trp Ser Val Gly Cys Ile Met Ala Glu Met Val Leu His Lys Val Leu
    210                 215                 220

Phe Pro Gly Arg Asp Tyr Ile Asp Gln Trp Asn Lys Val Ile Glu Gln
225                 230                 235                 240

Leu Gly Thr Pro Ser Ala Glu Phe Met Lys Lys Leu Gln Pro Thr Val
                245                 250                 255

Arg Asn Tyr Val Glu Asn Arg Pro Lys Tyr Pro Gly Ile Lys Phe Glu
                260                 265                 270

Glu Leu Phe Pro Asp Trp Ile Phe Pro Ser Glu Ser Glu Arg Asp Lys
            275                 280                 285

Ile Lys Thr Ser Gln Ala Arg Asp Leu Leu Ser Lys Met Leu Val Ile
    290                 295                 300

Asp Pro Asp Lys Arg Ile Ser Val Asp Glu Ala Leu Arg His Pro Tyr
305                 310                 315                 320

Ile Thr Val Trp Tyr Asp Pro Ala Glu Ala Glu Ala Pro Pro Pro Gln
                325                 330                 335

Ile Tyr Asp Ala Gln Leu Glu Glu Arg Glu His Ala Ile Glu Glu Trp
            340                 345                 350

Lys Glu Leu Ile Tyr Lys Glu Val Met Asp Trp Glu Glu Arg Ser Lys
    355                 360                 365

Asn Gly Val Val Lys Asp Gln Pro Ser Ala Gln Met Gln Gln
    370                 375                 380

(2) INFORMATION FOR SEQ ID NO:31:

(i) SEQUENCE CHARACTERISTICS:
        (A) LENGTH: 424 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

Met Ser Asp Ser Lys Cys Asp Ser Gln Phe Tyr Ser Val Gln Val Ala
 1               5                  10                  15
```

-continued

```
Asp Ser Thr Phe Thr Val Leu Lys Arg Tyr Gln Gln Leu Lys Pro Ile
         20                  25                  30

Gly Ser Gly Ala Gln Gly Ile Val Cys Ala Ala Phe Asp Thr Val Leu
         35                  40                  45

Gly Ile Ser Val Ala Val Lys Lys Leu Ser Arg Pro Phe Gln Asn Gln
         50                  55                  60

Thr His Ala Lys Arg Ala Tyr Arg Glu Leu Val Leu Leu Lys Cys Val
 65                  70                  75                  80

Asn His Lys Asn Ile Ile Ser Leu Leu Asn Val Phe Thr Pro Gln Lys
                     85                  90                  95

Thr Leu Glu Glu Phe Gln Asp Val Tyr Leu Val Met Glu Leu Met Asp
            100                 105                 110

Ala Asn Leu Cys Gln Val Ile His Met Glu Leu Asp His Glu Arg Met
            115                 120                 125

Ser Tyr Leu Leu Tyr Gln Met Leu Cys Gly Ile Lys His Leu His Ser
            130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Cys Thr Asn Phe Met Met Thr Pro Tyr Val Val Thr Arg Tyr Tyr Arg
                180                 185                 190

Ala Pro Glu Val Ile Leu Gly Met Gly Tyr Lys Glu Asn Val Asp Ile
            195                 200                 205

Trp Ser Val Gly Cys Ile Met Ala Glu Met Val Leu His Lys Val Leu
    210                 215                 220

Phe Pro Gly Arg Asp Tyr Ile Asp Gln Trp Asn Lys Val Ile Glu Gln
225                 230                 235                 240

Leu Gly Thr Pro Ser Ala Glu Phe Met Lys Lys Leu Gln Pro Thr Val
                245                 250                 255

Arg Asn Tyr Val Glu Asn Arg Pro Lys Tyr Pro Gly Ile Lys Phe Glu
            260                 265                 270

Glu Leu Phe Pro Asp Trp Ile Phe Pro Ser Glu Ser Glu Arg Asp Lys
            275                 280                 285

Ile Lys Thr Ser Gln Ala Arg Asp Leu Leu Ser Lys Met Leu Val Ile
    290                 295                 300

Asp Pro Asp Lys Arg Ile Ser Val Asp Glu Ala Leu Arg His Pro Tyr
305                 310                 315                 320

Ile Thr Val Trp Tyr Asp Pro Ala Glu Ala Glu Ala Pro Pro Pro Gln
                325                 330                 335

Ile Tyr Asp Ala Gln Leu Glu Glu Arg Glu His Ala Ile Glu Glu Trp
            340                 345                 350

Lys Glu Leu Ile Tyr Lys Glu Val Met Asp Trp Glu Glu Arg Ser Lys
            355                 360                 365

Asn Gly Val Val Lys Asp Gln Pro Ser Asp Ala Ala Val Ser Ser Asn
    370                 375                 380

Ala Thr Pro Ser Gln Ser Ser Ile Asn Asp Ile Ser Ser Met Ser
385                 390                 395                 400

Thr Glu Gln Thr Leu Ala Ser Asp Thr Asp Ser Ser Leu Asp Ala Ser
                405                 410                 415

Thr Gly Pro Leu Glu Gly Cys Arg
            420
```

(2) INFORMATION FOR SEQ ID NO:32:

(i) SEQUENCE CHARACTERISTICS:
        (A) LENGTH: 424 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

```
Met Ser Asp Ser Lys Cys Asp Ser Gln Phe Tyr Ser Val Gln Val Ala
1               5                  10                  15

Asp Ser Thr Phe Thr Val Leu Lys Arg Tyr Gln Gln Leu Lys Pro Ile
            20                  25                  30

Gly Ser Gly Ala Gln Gly Ile Val Cys Ala Ala Phe Asp Thr Val Leu
        35                  40                  45

Gly Ile Asn Val Ala Val Lys Lys Leu Ser Arg Pro Phe Gln Asn Gln
    50                  55                  60

Thr His Ala Lys Arg Ala Tyr Arg Glu Leu Val Leu Leu Lys Cys Val
65                  70                  75                  80

Asn His Lys Asn Ile Ile Ser Leu Leu Asn Val Phe Thr Pro Gln Lys
                85                  90                  95

Thr Leu Glu Glu Phe Gln Asp Val Tyr Leu Val Met Glu Leu Met Asp
            100                 105                 110

Ala Asn Leu Cys Gln Val Ile His Met Glu Leu Asp His Glu Arg Met
        115                 120                 125

Ser Tyr Leu Leu Tyr Gln Met Leu Cys Gly Ile Lys His Leu His Ser
    130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Cys Thr Asn Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Ile
        195                 200                 205

Trp Ser Val Gly Cys Ile Met Gly Glu Leu Val Lys Gly Cys Val Ile
    210                 215                 220

Phe Gln Gly Thr Asp His Ile Asp Gln Trp Asn Lys Val Ile Glu Gln
225                 230                 235                 240

Leu Gly Thr Pro Ser Ala Glu Phe Met Lys Lys Leu Gln Pro Thr Val
                245                 250                 255

Arg Asn Tyr Val Glu Asn Arg Pro Lys Tyr Pro Gly Ile Lys Phe Glu
            260                 265                 270

Glu Leu Phe Pro Asp Trp Ile Phe Pro Ser Glu Ser Glu Arg Asp Lys
        275                 280                 285

Ile Lys Thr Ser Gln Ala Arg Asp Leu Leu Ser Lys Met Leu Val Ile
    290                 295                 300

Asp Pro Asp Lys Arg Ile Ser Val Asp Glu Ala Leu Arg His Pro Tyr
305                 310                 315                 320

Ile Thr Val Trp Tyr Asp Pro Ala Glu Ala Glu Ala Pro Pro Pro Gln
                325                 330                 335

Ile Tyr Asp Ala Gln Leu Glu Glu Arg Glu His Ala Ile Glu Glu Trp
            340                 345                 350

Lys Glu Leu Ile Tyr Lys Glu Val Met Asp Trp Glu Glu Arg Ser Lys
```

355                 360                 365
Asn Gly Val Val Lys Asp Gln Pro Pro Asp Ala Ala Val Ser Ser Asn
    370                 375                 380

Ala Thr Pro Ser Gln Ser Ser Ser Ile Asn Asp Ile Ser Ser Met Ser
385                 390                 395                 400

Thr Glu Gln Thr Leu Ala Ser Asp Thr Asp Ser Ser Leu Asp Ala Ser
                405                 410                 415

Thr Gly Pro Leu Glu Gly Cys Arg
                420

(2) INFORMATION FOR SEQ ID NO:33:

(i) SEQUENCE CHARACTERISTICS:
        (A) LENGTH: 384 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
                20                  25                  30

Gly Ser Gly Ala Gln Gly Ile Val Cys Ala Ala Tyr Asp Ala Ile Leu
            35                  40                  45

Glu Arg Asn Val Ala Ile Lys Lys Leu Ser Arg Pro Phe Gln Asn Gln
50                  55                  60

Thr His Ala Lys Arg Ala Tyr Arg Glu Leu Val Leu Met Lys Cys Val
65                  70                  75                  80

Asn His Lys Asn Ile Ile Gly Leu Leu Asn Val Phe Thr Pro Gln Lys
                85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
        115                 120                 125

Ser Tyr Leu Leu Tyr Gln Met Leu Cys Gly Ile Lys His Leu His Ser
    130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Leu
        195                 200                 205

Trp Ser Val Gly Cys Ile Met Gly Glu Met Val Cys His Lys Ile Leu
    210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
                245                 250                 255

Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys

```
                275                 280                 285
Leu Lys Ala Ser Gln Ala Arg Asp Leu Leu Ser Lys Met Leu Val Ile
            290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
            325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
            355                 360                 365

Asn Gly Val Ile Arg Gly Gln Pro Ser Pro Leu Ala Gln Val Gln Gln
            370                 375                 380

(2) INFORMATION FOR SEQ ID NO:34:

(i) SEQUENCE CHARACTERISTICS:
        (A) LENGTH: 427 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
            20                  25                  30

Gly Ser Gly Ala Gln Gly Ile Val Cys Ala Ala Tyr Asp Ala Ile Leu
        35                  40                  45

Glu Arg Asn Val Ala Ile Lys Lys Leu Ser Arg Pro Phe Gln Asn Gln
50                  55                  60

Thr His Ala Lys Arg Ala Tyr Arg Glu Leu Val Leu Met Lys Cys Val
65                  70                  75                  80

Asn His Lys Asn Ile Ile Gly Leu Leu Asn Val Phe Thr Pro Gln Lys
            85                  90                  95

Ser Leu Glu Glu Phe Gln Asp Val Tyr Ile Val Met Glu Leu Met Asp
        100                 105                 110

Ala Asn Leu Cys Gln Val Ile Gln Met Glu Leu Asp His Glu Arg Met
        115                 120                 125

Ser Tyr Leu Leu Tyr Gln Met Leu Cys Gly Ile Lys His Leu His Ser
        130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Leu
        195                 200                 205

Trp Ser Val Gly Cys Ile Met Gly Glu Met Val Cys His Lys Ile Leu
        210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
```

```
                    245                 250                 255
Arg Thr Tyr Val Glu Asn Arg Pro Lys Tyr Ala Gly Tyr Ser Phe Glu
                260                 265                 270

Lys Leu Phe Pro Asp Val Leu Phe Pro Ala Asp Ser Glu His Asn Lys
            275                 280                 285

Leu Lys Ala Ser Gln Ala Arg Asp Leu Leu Ser Lys Met Leu Val Ile
        290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
        355                 360                 365

Asn Gly Val Ile Arg Gly Gln Pro Ser Pro Leu Gly Ala Ala Val Ile
    370                 375                 380

Asn Gly Ser Gln His Pro Ser Ser Ser Ser Val Asn Asp Val Ser
385                 390                 395                 400

Ser Met Ser Thr Asp Pro Thr Leu Ala Ser Asp Thr Asp Ser Ser Leu
                405                 410                 415

Glu Ala Ala Gly Pro Leu Gly Cys Cys Arg
            420                 425

(2) INFORMATION FOR SEQ ID NO:35:

(i) SEQUENCE CHARACTERISTICS:
        (A) LENGTH: 384 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
            20                  25                  30

Gly Ser Gly Ala Gln Gly Ile Val Cys Ala Ala Tyr Asp Ala Ile Leu
        35                  40                  45

Glu Arg Asn Val Ala Ile Lys Lys Leu Ser Arg Pro Phe Gln Asn Gln
50                  55                  60

Thr His Ala Lys Arg Ala Tyr Arg Glu Leu Val Leu Met Lys Cys Val
65                  70                  75                  80

Asn His Lys Asn Ile Ile Gly Leu Leu Asn Val Phe Thr Pro Gln Lys
                85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
        115                 120                 125

Ser Tyr Leu Leu Tyr Gln Met Leu Cys Gly Ile Lys His Leu His Ser
    130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
```

-continued

```
                165                 170                 175
Gly Thr Ser Phe Met Met Thr Pro Tyr Val Thr Arg Tyr Tyr Arg
            180                 185                 190
Ala Pro Glu Val Ile Leu Gly Met Gly Tyr Lys Glu Asn Val Asp Ile
        195                 200                 205
Trp Ser Val Gly Cys Ile Met Gly Glu Met Ile Lys Gly Gly Val Leu
    210                 215                 220
Phe Pro Gly Thr Asp His Ile Asp Gln Trp Asn Lys Val Ile Glu Gln
225                 230                 235                 240
Leu Gly Thr Pro Cys Pro Glu Phe Met Lys Lys Leu Gln Pro Thr Val
            245                 250                 255
Arg Thr Tyr Val Glu Asn Arg Pro Lys Tyr Ala Gly Tyr Ser Phe Glu
        260                 265                 270
Lys Leu Phe Pro Asp Val Leu Phe Pro Ala Asp Ser Glu His Asn Lys
    275                 280                 285
Leu Lys Ala Ser Gln Ala Arg Asp Leu Leu Ser Lys Met Leu Val Ile
290                 295                 300
Asp Ala Ser Lys Arg Ile Ser Val Asp Glu Ala Leu Gln His Pro Tyr
305                 310                 315                 320
Ile Asn Val Trp Tyr Asp Pro Ser Glu Ala Glu Ala Pro Pro Lys
            325                 330                 335
Ile Pro Asp Lys Gln Leu Asp Glu Arg Glu His Thr Ile Glu Glu Trp
        340                 345                 350
Lys Glu Leu Ile Tyr Lys Glu Val Met Asp Leu Glu Glu Arg Thr Lys
            355                 360                 365
Asn Gly Val Ile Arg Gly Gln Pro Ser Pro Leu Ala Gln Val Gln Gln
370                 375                 380
```

(2) INFORMATION FOR SEQ ID NO:36:

(i) SEQUENCE CHARACTERISTICS:
        (A) LENGTH: 427 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:36:

```
Met Ser Arg Ser Lys Arg Asp Asn Asn Phe Tyr Ser Val Glu Ile Gly
1               5                   10                  15
Asp Ser Thr Phe Thr Val Leu Lys Arg Tyr Gln Asn Leu Lys Pro Ile
            20                  25                  30
Gly Ser Gly Ala Gln Gly Ile Val Cys Ala Ala Tyr Asp Ala Ile Leu
        35                  40                  45
Glu Arg Asn Val Ala Ile Lys Lys Leu Ser Arg Pro Phe Gln Asn Gln
    50                  55                  60
Thr His Ala Lys Arg Ala Tyr Arg Glu Leu Val Leu Met Lys Cys Val
65                  70                  75                  80
Asn His Lys Asn Ile Ile Gly Leu Leu Asn Val Phe Thr Pro Gln Lys
                85                  90                  95
Ser Leu Glu Glu Phe Gln Asp Val Tyr Ile Val Met Glu Leu Met Asp
            100                 105                 110
Ala Asn Leu Cys Gln Val Ile Gln Met Glu Leu Asp His Glu Arg Met
        115                 120                 125
Ser Tyr Leu Leu Tyr Gln Met Leu Cys Gly Ile Lys His Leu His Ser
```

-continued

```
            130                 135                 140
Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
                180                 185                 190

Ala Pro Glu Val Ile Leu Gly Met Gly Tyr Lys Glu Asn Val Asp Ile
                195                 200                 205

Trp Ser Val Gly Cys Ile Met Gly Glu Met Ile Lys Gly Gly Val Leu
                210                 215                 220

Phe Pro Gly Thr Asp His Ile Asp Gln Trp Asn Lys Val Ile Glu Gln
225                 230                 235                 240

Leu Gly Thr Pro Cys Pro Glu Phe Met Lys Lys Leu Gln Pro Thr Val
                245                 250                 255

Arg Thr Tyr Val Glu Asn Arg Pro Lys Tyr Ala Gly Tyr Ser Phe Glu
                260                 265                 270

Lys Leu Phe Pro Asp Val Leu Phe Pro Ala Asp Ser Glu His Asn Lys
                275                 280                 285

Leu Lys Ala Ser Gln Ala Arg Asp Leu Leu Ser Lys Met Leu Val Ile
                290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                325                 330                 335

Ile Pro Asp Lys Gln Leu Asp Glu Arg Glu His Thr Ile Glu Glu Trp
                340                 345                 350

Lys Glu Leu Ile Tyr Lys Glu Val Met Asp Leu Glu Glu Arg Thr Lys
                355                 360                 365

Asn Gly Val Ile Arg Gly Gln Pro Ser Pro Leu Gly Ala Ala Val Ile
                370                 375                 380

Asn Gly Ser Gln His Pro Ser Ser Ser Ser Val Asn Asp Val Ser
385                 390                 395                 400

Ser Met Ser Thr Asp Pro Thr Leu Ala Ser Asp Thr Asp Ser Ser Leu
                405                 410                 415

Glu Ala Ala Gly Pro Leu Gly Cys Cys Arg
                420                 425
```

(2) INFORMATION FOR SEQ ID NO:37:

(i) SEQUENCE CHARACTERISTICS:
        (A) LENGTH: 364 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:37:

```
Met Ser Gly Pro Arg Ala Gly Phe Tyr Arg Gln Glu Leu Asn Lys Thr
1               5                   10                  15

Val Trp Glu Val Pro Gln Arg Leu Gln Gly Leu Arg Pro Val Gly Ser
                20                  25                  30

Gly Ala Tyr Gly Ser Val Cys Ser Ala Tyr Asp Ala Arg Leu Arg Gln
                35                  40                  45

Lys Val Ala Val Lys Lys Leu Ser Arg Pro Phe Gln Ser Leu Ile His
```

-continued

```
              50                  55                  60
Ala Arg Arg Thr Tyr Arg Glu Leu Arg Leu Leu Lys His Leu Lys His
 65                  70                  75                  80
Glu Asn Val Ile Gly Leu Leu Asp Val Phe Thr Pro Ala Thr Ser Ile
                 85                  90                  95
Glu Asp Phe Ser Glu Val Tyr Leu Val Thr Thr Leu Met Gly Ala Asp
                100                 105                 110
Leu Asn Asn Ile Val Lys Cys Gln Ala Leu Ser Asp Glu His Val Gln
                115                 120                 125
Phe Leu Val Tyr Gln Leu Leu Arg Gly Leu Lys Tyr Ile His Ser Ala
            130                 135                 140
Gly Ile Ile His Arg Asp Leu Lys Pro Ser Asn Val Ala Val Asn Glu
145                 150                 155                 160
Asp Cys Glu Leu Arg Ile Leu Asp Phe Gly Leu Ala Arg Gln Ala Asp
                165                 170                 175
Glu Glu Met Thr Gly Tyr Val Ala Thr Arg Trp Tyr Arg Ala Pro Glu
                180                 185                 190
Ile Met Leu Asn Trp Met His Tyr Asn Gln Thr Val Asp Ile Trp Ser
            195                 200                 205
Val Gly Cys Ile Met Ala Glu Leu Leu Gln Gly Lys Ala Leu Phe Pro
            210                 215                 220
Gly Ser Asp Tyr Ile Asp Gln Leu Lys Arg Ile Met Glu Val Val Gly
225                 230                 235                 240
Thr Pro Ser Pro Glu Val Leu Ala Lys Ile Ser Ser Glu His Ala Arg
                245                 250                 255
Thr Tyr Ile Gln Ser Leu Pro Pro Met Pro Gln Lys Asp Leu Ser Ser
                260                 265                 270
Ile Phe Arg Gly Ala Asn Pro Leu Ala Ile Asp Leu Leu Gly Arg Met
            275                 280                 285
Leu Val Leu Asp Ser Asp Gln Arg Val Ser Ala Ala Glu Ala Leu Ala
            290                 295                 300
His Ala Tyr Phe Ser Gln Tyr His Asp Pro Glu Asp Glu Pro Glu Ala
305                 310                 315                 320
Glu Pro Tyr Asp Glu Gly Val Glu Ala Lys Glu Arg Thr Leu Glu Glu
                325                 330                 335
Trp Lys Glu Leu Thr Tyr Gln Glu Val Leu Ser Phe Lys Pro Pro Glu
            340                 345                 350
Pro Pro Lys Pro Pro Gly Ser Leu Glu Ile Glu Gln
            355                 360
```

METHODS FOR DESIGNING INHIBITORS OF SERINE/THREONINE-KINASES AND TYROSINE KINASES

TECHNICAL FIELD OF INVENTION

The invention relates to methods for designing inhibitors of serine/threonine kinases, particularly MAP kinases, and tyrosine kinases through the use of ATP-binding site mutants of those kinases. The methods of this invention take advantage of the fact that the mutant kinases are capable of binding inhibitory compounds of other kinases with greater affinity than the corresponding wild-type kinase. The invention further relates to the mutant kinases themselves and crystallizable co-complexes of the mutant kinase and the inhibitory compound.

BACKGROUND OF THE INVENTION

Kinases and protein kinase cascades are involved in most cell signaling pathways, and many of these pathways play a role in human disease. For instance, kinases have been implicated in cell entry into apoptosis [P. Anderson, *Micobiol. Mol. Biol. Rev.*, 61, pp. 33–46 (1997)], cancer [P. Dirks, *Neurosurgery*, 40, pp. 1000–13, (1997)], Alzheimer's disease [K. Imahori et al., *J. Biochem.*, 121, pp. 179–88 (1997)] angiotensin II and hematopoietic cytokine receptor signal transduction [B. Berk et al., *Circ. Res.*, 80:5, pp. 607–16 (1997); R. Mufson, *FASEB J.*, 11:1 pp. 37–44 (1997)], oncoprotein signaling and mitosis [A. Laird et al., *Cell Signal*, 9:3–4 pp. 249–55 (1997)], inflammation and infection [J. Han et al., *Nature*, 386 296–9 (1997).] An understanding of the structure, function, and inhibition of kinase activity could lead to useful human therapeutics.

The structures of a number of protein kinases have been solved by X-ray diffraction and analyzed [reviewed in L. Johnson et al., *Cell*, 85, pp. 149–158 (1996); E. Goldsmith et al., *Cur. Opin. Struct. Biol.*, 4, pp. 833–840 (1994); S. Taylor et al., *Structure*, 2, pp. 345–355 (1994)]. Enzymes in the kinase family are often characterized by two domains separated by a deep channel. The N-terminal domain creates a binding pocket for the adenine ring of ATP, and the C-terminal domain contains the presumed catalytic base, magnesium binding sites, and phosphorylation lip. Sequence homology among the kinases varies, but is usually highest in the ATP-binding site. ATP is a substrate common for all kinases.

Among medically important tyrosine kinases are epidermal growth factor receptor (EGFR), platelet-derived growth factor receptor (PDGFR), fibroblast growth factor receptor (FGFR), Flk-1, and src.

One particularly important class of serine/threonine kinases are the mammalian mitogen-activated protein (MAP)1 kinases. These kinases mediate intracellular signal transduction pathways [M. H. Cobb et al., *J. Biol. Chem.*, 270, pp. 14843–6 (1995); R. J. Davis, *Mol. Reprod. Dev.*, 42, pp. 459–67 (1995)]. Members of the MAP kinase family share sequence similarity and conserved structural domains, and include the extracellular-signal regulated kinases (ERKs), Jun N-terminal kinases (JNKs) and p38 kinases. JNK and p38 kinases are activated in response to the pro-inflammatory cytokines TNF-α and interleukin-1, and by cellular stress such as heat shock, hyperosmolarity, ultraviolet radiation, lipopolysaccharides and inhibitors of protein synthesis [B. Derijard et al., *Cell*, 76, pp. 1025–37 (1994); J. Han et al., *Science*, 265, pp. 808–11 (1994); J. Raingeaud et al., *J. Biol. Chem.*, 270, pp. 7420–6 (1995); L. Shapiro et al., *Proc. Natl. Acad. Sci. U.S.A.*, 92, pp. 12230–4 (1995)]. In contrast, ERK kinases are activated by mitogens and growth factors [D. Bokemeyer et al., *Kidney Int.*, 49, pp. 1187–98 (1996)].

ERK2 is found in many different cell types. ERK2 is a protein kinase that achieves maximum activity when both Thr183 and Tyr185 are phosphorylated by the upstream MAP kinase kinase, MEK1 [N. G. Anderson et al., *Nature*, 343, pp. 651–3 (1990); C. M. Crews et al., *Science*, 258, pp. 478–80 (1992)]. Upon activation, ERK2 phosphorylates many regulatory proteins, including the protein kinases Rsk90 [C. Bjorbaek et al., *J. Biol. Chem.* 270, pp. 18848–52 (1995)] and MAPKAP2 [J. Rouse et al., *Cell*, 78, pp. 1027–37 (1994)], and transcription factors such as ATF2 [J. Raingeaud et al., *Mol. Cell. Biol.*, 16, pp. 1247–55 (1996)], Elk-1 [J. Raingeaud et al. (1996)], c-Fos [R. H. Chen et al., *Proc. Natl. Acad. Sci. U.S.A.*, 90, pp. 10952–6 (1993)], and c-Myc [B. L. Oliver et al., *Proc. Soc. Exp. Biol. Med.*, 210, pp. 162–70 (1995)]. ERK2 is also a downstream target of the Ras/Raf dependent pathways [S. A. Moodie et al., *Science*, 260, pp. 1658–61 (1993)] and may help relay the signals from these potentially oncogenic proteins. ERK2 has been shown to play a role in the negative growth control of breast cancer cells [R. S. Frey et al., *Cancer Res.*, 57, pp. 628–33 (1997)] and hyperexpression of ERK2 in human breast cancer has been reported [V. S. Sivaraman et al., *J. Clin. Invest.*, 99, pp. 1478–83 (1997)]. Activated ERK2 has also been implicated in the proliferation of endothelin-stimulated airway smooth muscle cells, suggesting a role for this kinase in asthma [A. Whelchel et al., *Am. J. Respir. Cell. Mol. Biol.*, 16, pp. 589–96 (1997)]. In addition, ERK2 appears to be involved in platelet-derived growth factor-directed migration of vascular smooth muscle cells, suggesting that this kinase may be also be involved in restenosis and hypertension. [K. Graf et al., *Hypertension*, 29:1, pp. 334–339 (1997)].

The crystal structures of unphosphorylated p38 [K. P. Wilson et al., *J. Biol. Chem.*, 271, pp. 27696–700 (1996); Z. Wang et al., *Proc. Natl. Acad. Sci. U.S.A.*, 94, pp. 2327–32 (1997);(Brookhaven PDB entry, 1WFC)], and ERK2 [F. Zhang et al., *Nature*, 367, pp. 704–11 (1994); (Brookhaven PDB entry, 1ERK)] have been solved. Recently, a phosphorylated ERK2 crystal structure has also been solved [B. J. Canagarajah et al., *Cell*, 90, pp. 859–69 (1997)]. The fold and topology of ERK2 is similar to p38 [K. P. Wilson et al. (1996)], and the two proteins are 48% identical in amino acid sequence.

p38 was identified as a kinase that was phosphorylated on tyrosine following stimulation of monocytes by LPS [J. C. Lee et al., *Nature*, 372, pp. 739–46 (1994)]. p38 kinase was cloned [J. Han et al. (1994)] and shown to be the target for pyridinylimidazole compounds that block the production of IL-1β and TNF-α by monocytes stimulated with LPS [J. C. Lee et al. (1994)]. SB203580, a 2,4,5-triarylimidazole, is a potent p38 kinase inhibitor that is selective relative to other kinases, including other closely related MAP kinases [A. Cuenda et al., *FEBS Lett.*, 364, pp. 229–33 (1995); A. Cuenda et al., *EMBO J.*, 16, pp. 295–305 (1997)]. The structure of SB203580 in complex with p38 has been reported [L. Tong et al., *Nat. Struct. Biol.*, 4, pp. 311–6 (1997)]. The crystal structure of a different pyridinylimidazole compound, VK-19,911, 4-(4-fluorophenyl)-1-(4-piperidinyl)-5-(4-pyridyl)-imidazole in complex with p38 has also been described [K. P. Wilson et al., *Chem. & Biol.*, 4, pp. 223–231 (1997)]. These structures identified the residues important for binding pyridinyl-imidazoles, and revealed that both compounds bind within the ATP binding site of p38. Many of these residues are conserved in ERK2, but there are enough differences that binding of pyridinyl-imidazole compounds does not occur. A similar situation exists for JNK3, which also shares structural similarity to p38, but is unable to bind pyridinyl-imidazole inhibitors. This same type of scenario, wherein a compound binds to one family member, but not to the majority of others, is also likely to occur in other serine/threonine kinase and tyrosine kinase families.

However, the kinase family members that do not share affinity for a compound that binds to one member may be equally, if not more important from a medical standpoint. Thus, there is an ongoing need to identify potential inhibitors of those other kinases.

SUMMARY OF THE INVENTION

The present invention solves the problem indicated above by providing a method of identifying potential inhibitors of serine/threonine kinases and tyrosine kinases that are related to a kinase which has a known inhibitor. In particular, the invention provides a method of identifying potential inhibitors of ERK2 and JNK3, as well as other MAP kinases that are unable to bind pyridinylimidazole compounds which inhibit the MAP kinase p38.

The method of the present invention is based upon the identification of residues in the ATP-binding pocket of a first kinase that make close contacts with an inhibitor. This may be achieved by crystallizing a first kinase with a known inhibitor and analyzing the data. Alternatively, such data may already be available.

Once this information is provided, related kinases are identified using readily available protein alignment software and databases of proteins. Related kinases which share some, but not all, of the first kinase ATP binding pocket amino acid residues that interact with the known inhibitor are selected as candidates for which new inhibitors may be designed.

One or more of the amino acid residues in the ATP binding pocket of the related ("second") kinase which could potentially interact with the known inhibitor, but which are different from the corresponding amino acid residue in the first kinase are then altered to increase affinity for the known inhibitor. This "mutated" or "mutant" second kinase is also part of the present invention. The ability of the known inhibitor to bind to the mutant second kinase with good affinity is confirmed by binding studies.

Once affinity is confirmed, the mutant second kinase-known inhibitor complex is subjected to molecular modeling means (X-ray crystallography, 3-D computer analysis) to determine how to alter the known inhibitor to create a compound which inhibits the wild type second kinase.

The crystallizable co-complex of the mutant second kinase with the known inhibitor is also a part of this invention.

DETAILED DESCRIPTION OF THE INVENTION

According to one embodiment, the invention provides a method for designing an inhibitor of a second serine/threonine kinase or a second tyrosine kinase. This method comprises the steps of:

a. identifying amino acids in an ATP binding site of a first serine/threonine kinase or a first tyrosine kinase which form close contacts with a compound bound to said ATP binding site;

b. employing protein alignment means to identify a second serine/threonine kinase or a second tyrosine kinase that form some, but not all, of the close contacts formed between said compound and said first serine/threonine kinase or said first tyrosine kinase;

c. altering an amino acid in the ATP binding site of said second serine/threonine kinase or said second tyrosine kinase to create a mutant second serine/threonine kinase or a mutant second tyrosine kinase, wherein said compound binds with at least 10-fold greater affinity to said mutant second kinase than to said second kinase;

d. confirming that said compound binds with greater affinity to said mutant second serine/threonine kinase or said mutant second tyrosine kinase than to said second serine/threonine kinase or said second tyrosine kinase; and e. using molecular modeling means to modify said compound to create an inhibitor of said second kinase, such that said inhibitor binds to said second kinase with at least 10-fold greater affinity than said compound binds to said second kinase.

The identification of the amino acids in an ATP binding site of a first serine/threonine kinase or a first tyrosine kinase which form close contacts with a compound bound to said ATP binding site is routinely performed by analyzing the X-ray crystal structure of the first kinase co-complexed with an inhibitor that is known to bind to its ATP binding site, or co-complexed with ATP itself.

Standard X-ray crystallographic techniques, equipment and software are used to generate crystals of the co-complex, carry out the X-ray diffraction, collect and analyze the data. These techniques, equipment and software are well known in the art.

It should be understood, however, that generating the X-ray data is not a required step in the method of this invention. One may begin by having this data (either raw or fully analyzed) in hand from previous experiments or from an outside source. One may also begin by acquiring the knowledge of which amino acids make close contact with the bound inhibitor or ATP directly from another source.

The term "close contact", as used herein, means that an atom or atoms of the ATP binding site of the kinase are physically close enough to an atom or atoms of the compound bound to that site and that the atoms are of such a nature as to enable the formation of non-covalent bonds, such as hydrogen bonds or van der Waals or electrostatic interactions. Physical distances of less than 4 Å are required to form significant non-covalent interactions. A close contact also includes any covalent interactions between the kinase and the ligand.

The choice of inhibitor to bind to the kinase in order to generate information on close contacts depends upon the nature of the kinase. The inhibitor should bind tightly to the kinase and significantly inhibit the ability of the kinase to hydrolyze ATP. Any known inhibitor that has a $K_d$ and/or a $K_i$ of less than 1 μM will suffice. Preferably, the inhibitor will have a $K_d$ and/or a $K_i$ of less than 100 nM.

The measurements of $K_i$ for enzyme inhibition and $K_d$ for binding of a ligand to a protein of interest are well known in the art. These are described, for example, in "Enzyme Structure and Mechanism, Second Edition," Alan Fersht, ed., W. H. Freeman and Company, New York (1985), the disclosure of which is herein incorporated by reference.

According to a preferred embodiment, the first kinase is a MAP kinase. Even more preferred is that the first kinase be p38 having the amino acid sequence set forth in SEQ ID NO:1. Preferably, the inhibitor bound to p38 of SEQ ID NO:1 is a pyridinyl-imidazole compound.

More preferably, the pyridinyl-imidazole compound is selected from SB203580 or SB 202190, which have the structures depicted below.

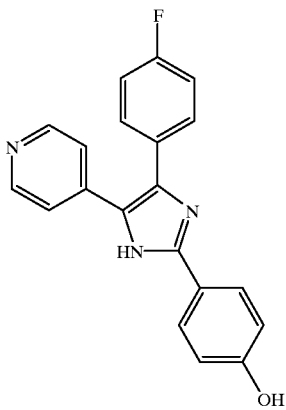

SB 202190

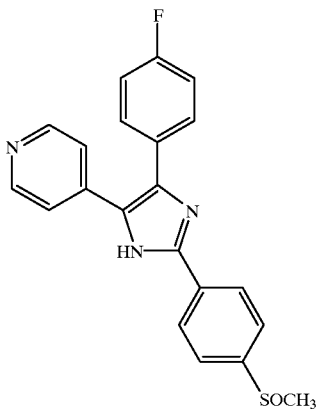

SB 203580

Other pyridinyl-imidazole compounds that may be useful to co-complex with p38 are described in U.S. Pat. Nos. 5,670,527 and 5,658,903, the disclosures of which are herein incorporated by reference.

Once the close contact amino acids have been identified, the next step is to identify a second serine/threonine kinase or tyrosine kinase that forms some, but not all, of the close contacts formed between the ligand and the first kinase. This is achieved by employing protein alignment means comparing the amino acid sequence of the first kinase with a database containing other kinase amino acid sequences, such as GenBank.

Protein alignment means involve the use of computer software that performs a best fit alignment of a first protein with another, related protein. Several state-of-art computer programs are available for homology comparison and alignment of structure- and sequence-related proteins.

One example of homology alignment program is PILEUP (Genetics Computer Group) which compares multiple sequences of related proteins and nucleotides and generates an alignment of these sequences for comparison.

PILEUP allows one to use primary protein sequence similarity and structure similarity as parameters to set up an alignment of multiple proteins. Once the close contact amino acid residues of first kinase are defined, corresponding residues in the second kinase of interest can be identified from the alignment generated by the program.

From a practical consideration, the amino acid residues of the second kinase that align with the close contact amino acids of the first kinase should differ at a least 1 and not more than 4 residues.

Protein alignment means will identify related kinases and the amino acid residues thereof that align with the close contact amino acids of the first kinase and thus could potentially form close contacts with the inhibitor of the first kinase. The amino acids of this second kinase that align with the close contact amino acids of the first kinase, but differ in identity and/or nature therefrom, are the amino acids that will be targeted for replacement in the next step of the method. The term "nature" of an amino acid, as used herein, means its physicochemical characteristics, e.g., polar, non-polar, hydrophobic, hydrophilic, bulky side group, non-bulky side group, acidic, basic, etc.

According to one preferred embodiment, the second kinase is a MAP kinase. Even more preferred is that the second kinase be ERK-2 having the amino acid sequence set forth in SEQ ID NO:2, wherein amino acid 103 is isoleucine, amino acid 105 is glutamine, amino acid 106 is aspartic acid, amino acid 109 is glutamic acid and amino acid 110 is threonine; or JNK3 comprising at least amino acids 40–402 of SEQ ID NO:3, wherein amino acid 146 is methionine and amino acid 150 is aspartic acid.

Those particular amino acids will be changed to be identical to, or at least similar in nature to, the corresponding amino acid in the first kinase to create a mutant second kinase. This alteration will increase the ability of the ligand to bind to the second (now mutant) kinase by at least 10-fold over its affinity for the unmutated second kinase, as measured by $K_i$ or $K_d$. If the ligand has no detectable binding to the unmutated second kinase (and therefore a 10-fold increase may not be measurable), the ligand should bind to the mutated second kinase with a $K_i$ and/or $K_d$ of less than 10 $\mu$M.

The alteration of one or more amino acid in the ATP binding site of the second kinase according to the next step in the method may be achieved by standard molecular biological means. For example, site-directed mutagenesis, PCR, or other methods of altering the DNA or a cDNA encoding the second kinase is utilized to change an amino acid in that kinase to create a mutant second kinase. Obviously, the mutant kinase will be produced by recombinant DNA means, which are well known in the art.

In one preferred embodiment, the mutant second kinase is an ERK-2 mutant having the amino acid sequence set forth in SEQ ID NO:2, wherein amino acid 105 is threonine or alanine. According to another preferred embodiment, the mutant second kinase is an ERK-2 mutant having the amino acid sequence set forth in SEQ ID NO:2, wherein amino acid 105 is threonine or alanine, amino acid 103 is leucine, amino acid 106 is histidine, amino acid 109 is glycine and amino acid 110 is alanine. In this embodiment, although 5 amino acids have been changed as compared to naturally occurring ERK-2, only amino acid 105 is considered to be a close contact amino acid. The other altered amino acids were chosen based on proximity to amino acid 105 and because they differed from those present in p38.

In another preferred embodiment, the mutant second kinase is JNK3 mutant kinase comprising amino acids 40–402 of SEQ ID NO:3, wherein amino acid 146 is alanine. According to another preferred embodiment, the mutant second kinase is JNK3 mutant kinase comprising amino acids 40–402 of SEQ ID NO:3, wherein amino acid 146 is alanine and amino acid 150 is glycine.

Once the mutant second kinase has been created at the DNA level and expressed in an appropriate host cell and isolated, the next step of the method of this invention is to confirm its ability to bind to the ligand of the first kinase. This may be achieved by various methods well known in the art for determining $K_i$ and/or $K_d$.

The step following confirmation of binding between the ligand and the mutant second kinase is the modification of the ligand so that is capable of binding to and inhibiting the ATP binding site of the native form of the second kinase. This step is achieved using molecular modeling means that typically involve solving the crystal structure of the mutant second kinase/ligand co-complex; analyzing the contacts made between the co-complex components; comparing how the ligand would interact with the native second kinase using computer stimulation and the appropriate software; and altering those portions of the ligand that are sterically hindered from or otherwise incompatible with binding to the native second kinase. The software typically utilized in molecular modeling is capable of achieving each of these steps, as well as suggesting potential replacements for various moieties of the ligand that would increase association with the native second kinase.

One skilled in the art may use one of several methods to screen chemical moieties to replace portions of the ligand so that binding to the native second kinase is optimized. This process may begin by side-by-side visual inspection of, for example, native second kinase and the mutant second kinase ATP binding sites on the computer screen based on the X-ray structure of the ligand/mutant second kinase co-complex. Modified ligands may then be tested for their ability to dock to the native second kinase using software such as DOCK and AUTODOCK followed by energy minimization and molecular dynamics with standard molecular mechanics force fields, such as CHARMM and AMBER.

Specialized computer programs may also assist in the process of replacement fragments:
1. GRID (P. J. Goodford, "A Computational Procedure for Determining Energetically Favorable Binding Sites on Biologically Important Macromolecules", *J. Med. Chem.*, 28, pp. 849–857 (1985)). GRID is available from Oxford University, Oxford, UK.
2. MCSS (A. Miranker et al., "Functionality Maps of Binding Sites: A Multiple Copy Simultaneous Search Method." *Proteins: Structure, Function and Genetics*, 11, pp. 29–34 (1991)). MCSS is available from Molecular Simulations, Burlington, Mass.
3. AUTODOCK (D. S. Goodsell et al., "Automated Docking of Substrates to Proteins by Simulated Annealing", *Proteins: Structure, Function. and Genetics*, 8, pp. 195–202 (1990)). AUTODOCK is available from Scripps Research Institute, La Jolla, Calif.
4. DOCK (I. D. Kuntz et al., "A Geometric Approach to Macromolecule-Ligand Interactions", *J. Mol. Biol.*, 161, pp. 269–288 (1982)). DOCK is available from University of California, San Francisco, Calif.

Alternatively, the portion of the ligand that makes favorable contacts with the identical amino acids in both the mutant and the native second kinase may be retained as a scaffold and used in software programs that create theoretical inhibitors based upon the structure of the native second kinase ATP binding site. These programs include:
1. LUDI (H.-J. Bohm, "The Computer Program LUDI: A New Method for the De Novo Design of Enzyme Inhibitors", *J. Comp. Aid. Molec. Design*, 6, pp. 61–78 (1992)). LUDI is available from Biosym Technologies, San Diego, Calif.
2. LEGEND (Y. Nishibata et al., *Tetrahedron*, 47, p. 8985 (1991)). LEGEND is available from Molecular Simulations, Burlington, Mass.
3. LeapFrog (available from Tripos Associates, St. Louis, Mo.).

Other molecular modeling techniques may also be employed in accordance with this invention. See, e.g., N. C. Cohen et al., "Molecular Modeling Software and Methods for Medicinal Chemistry, *J. Med. Chem.*, 33, pp. 883–894 (1990). See also, M. A. Navia et al., "The Use of Structural Information in Drug Design", *Current Opinions in Structural Biology*, 2, pp. 202–210 (1992).

Once a compound has been designed or selected by the above methods, the efficiency with which that entity may bind to the native second kinase may be tested and further optimized by computational evaluation.

An entity designed or selected as binding to the native second kinase ATP binding pocket may be further computationally optimized so that in its bound state it would preferably lack repulsive electrostatic interaction with the target enzyme. Such non-complementary (e.g., electrostatic) interactions include repulsive charge-charge, dipole-dipole and charge-dipole interactions. Specifically, the sum of all electrostatic interactions between the inhibitor and the kinase when the inhibitor is bound to the ATP binding pocket preferably make a neutral or favorable contribution to the enthalpy of binding.

Specific computer software is available in the art to evaluate compound deformation energy and electrostatic interaction. Examples of programs designed for such uses include: Gaussian 92, revision C [M. J. Frisch, Gaussian, Inc., Pittsburgh, Pa. ©1992]; AMBER, version 4.0 [P. A. Kollman, University of California at San Francisco, ©1994]; QUANTA/CHARMM [Molecular Simulations, Inc., Burlington, Mass. ©1994]; and Insight II/Discover (Biosysm Technologies Inc., San Diego, Calif. ©1994). These programs may be implemented, for instance, using a Silicon Graphics workstation, Indigo$^2$ or IBM RISC/6000 workstation model 550. Other hardware systems and software packages will be known to those skilled in the art.

Once the second kinase ATP binding-pocket inhibitory entity has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. Such substituted chemical compounds may then be analyzed for efficiency of fit to the second kinase ATP binding pocket by the same computer methods described in detail, above.

According to another embodiment, the invention provides a mutant second kinase disclosed above. Such a kinase is enzymatically active in its ability to hydrolyze ATP and comprises an amino acid substitution (as compared to the native second kinase) that allows a compound that binds to the ATP binding site of a first serine/threonine kinase or tyrosine kinase to also bind to the ATP binding site of said second serine/threonine or tyrosine kinase. It is preferred that the ATP binding site of the native second kinase, which lacks the amino acid substitution present in the mutant, binds said compound with at least 10-fold lower affinity than said mutant kinase.

Preferably, the mutant kinase is an ERK-2 kinase having the amino acid sequence of SEQ ID NO:2, wherein amino acid 105 is threonine or alanine; or a mutant JNK3 kinase comprising amino acids 40–402 of SEQ ID NO:3, wherein amino acid 146 is alanine.

According to another preferred embodiment, both the native second kinase and the first kinase are MAP kinases.

More preferred is when the first kinase is p38 having the amino acid sequence of SEQ ID NO:1. Even more preferred is when the native second kinase is ERK-2 having the amino acid sequence of SEQ ID NO:2, wherein amino acid 103 is leucine, amino acid 106 is histidine, amino acid 109 is glycine amino acid 110 is alanine; or JNK3 comprising at least amino acids 40–402 of SEQ ID NO:3, wherein amino acid 146 is methionine and amino acid 150 is aspartic acid. The most preferred of these embodiments is wherein the compound that binds to the first kinase and the mutant second kinase is a pyridinyl-imidazole inhibitor of p38, preferably selected from SB203580 or SB202190.

After aligning the amino acid sequences of ERK2 and p38, we determined that there was a difference in amino acid type between aligned ERK2 amino acid 105 (glutamine) and p38 amino acid 106 (threonine) (see SEQ ID NOS: 1 and 2). Thus, we changed the ERK2 glutamine residue to an amino acid with a smaller side group, preferably threonine or alanine. The resulting mutant ERK2 enzyme retains its enzymatic activity and can bind a pyridinyl-imidazole inhibitor of p38.

The corresponding amino acids that need to be altered in other MAP kinases so that they bind pyridinyl-imidazole compounds with greater affinity can be identified by aligning its amino acid sequence with that of ERK2 and/or p38, as discussed above. The amino acid that aligns with amino acid T106 of p38 (SEQ ID NO:1) and Q105 of ERK2 (SEQ ID NO:2) is the one that will be targeted for substitution.

The ERK2 mutant containing the above-indicated amino acid substitution at amino acid 105 plus the following amino acid substitutions: isoleucine-to-leucine at amino acid 103, aspartic acid-to-histidine at amino acid 106, glutamic acid-to-glycine at amino acid 109 and threonine-to-alanine at amino acid 110; maintains its enzymatic activity, and binds more tightly to pyridinyl-imidazole compounds than the ERK2 with the single substitution at amino acid 105.

In corresponding fashion, we determined that in wild-type JNK3, amino acid 146 (methionine) (SEQ ID NO:3) aligned with Thr106 of p38. Thus, we changed the methionine residue to an alanine. The resulting JNK3 mutant retained its enzymatic activity and bound pyridinyl-imidazole compounds with at least 10-fold greater affinity than wild-type JNK3.

In order that the invention described herein may be more fully understood, the following examples are set forth. It should be understood that these examples are for illustrative purposes only and are not to be construed as limiting this invention in any manner.

EXAMPLE 1

Cloning, Mutagenesis And Expression of Kinases

A. p38

Expression, purification and activation of p38 MAP kinase was as described in K. P. Wilson et al., *Chem. & Biol.,* 4, pp. 223–231 (1997), the disclosure of which is herein incorporated by reference.

B. ERK2

Standard, well-known methods were used for manipulations of recombinant DNA. All subclones were verified by nucleotide sequence analysis of both strands using an Applied Biosystems 373A DNA Autosequencer).

An ERK2 cDNA was cloned by reverse transcription and subsequent polymerase chain reaction (RT-PCR) of total RNA (Qiagen) prepared from human peripheral lymphocytes (PBLs) which were stimulated with 10 ng/ml phorbol, 12-myristate,13-acetate (PMA) and 250 ng/ml ionomycin for 72 hours. The forward primer 5'-GAACGGCGGGCAGCCAACATGGCGGCGGCG-3' (SEQ ID NO:4) and the reverse primer 5'GGGCTCGAGC-CTGACAAATTTAAGATCTGTATCCTG-3' (SEQ ID NO:5) were used to generate an ERK2 PCR fragment (RNA PCR kit, Perkin-Elmer) which was cloned into pT7-Blue (Novagen) to yield pT7-ERK2.

For bacterial expression of recombinant ERK2, a (His)$_6$ metal affinity tag and a thrombin cleavage site were introduced at the N-terminus of the translation product. Simultaneously, NdeI and BamHI sites were added at the 5'-and 3'-end, respectively, by PCR using the forward primer 5'-TTAACATATGGCGGCGGCGGCGGCGGCG-3' (SEQ ID NO:6) and the reverse primer 5'-CCCACAGGATCCGATCTGTATCCTG-3' (Perkin-Elmer)(SEQ ID NO:7).

The NdeI-BamHI double-digested PCR fragment was cloned into the appropriate sites of pET-15b (Novagen) to yield pET-ERK2, which was used to transform *E. coli* BL21(DE3) (Novagen).

Freshly transformed bacteria were grown in LB broth supplemented with 100 μg/ml carbenicillin at 30° C. to an OD$_{600}$ of 0.7–0.9, induced with 1 mM isopropylthiogalactoside (IPTG) for 2 hours, harvested by low speed centrifugation and stored at −70° C. until use.

To facilitate construction of several ERK2 mutants, a silent mutation was introduced into the ERK2 cDNA that provided an additional, single HindIII restriction site near the region of mutations. This ERK2 variant (ERK2-HIII) and several ERK2 mutants were generated by PCR using PT7-ERK2 as template, a forward primer containing an internal SacII site (underlined), 5'-GATGGT CCGCGGGCAGGTGTTCG-3' (SEQ ID NO:8) and the following reverse primers containing a HindIII site (underlined) and one or several mutated nucleotides (bold letters):

(1) for ERK2-HIII 5'-GTGTCTTCAA AAGCTTGTAAAGATCTGTTTCC-3' (SEQ ID NO:9);

(2) for ERK2(Q103T) 5'-CAAAAGCTTGTAAAGATCTGTTTCCATGAGGTCC GTTACTAT-3' (SEQ ID NO:10)

(3) for ERK2(Q103A) 5'-CAA AAGCTTGTAAAGATCTGTTTCCATGAGGTCCG CTACTAT-3'(SEQ ID NO:11); and (4) for ERK2(I101L, Q103T, D104H, E107G, T108A), 5'-CAA AAGCTTGTAAAGATCTGCTCCCATGAGGTGCG TTACTAGATATAC-3' (SEQ ID NO:12). Each of these PCR fragments was digested with SacII and HindIII. Using the forward primer 5'-GATCTTTAC AAGCTTTTGAAGACACAAC-3' (SEQ ID NO:13) and reverse primer 5'-CTTGGTGTAGCCCTTGGAATTCAACATA-3' (SEQ ID NO:14), a second ERK2 PCR fragment was generated extending from the novel HindIII site to an MscI site. Ligation of the SacII-HindIII and HindIII-MscI PCR fragments into SacII-MscI double-digested pT7-ERK2 yielded pT7 subclones for the ERK2-HIII variant and all ERK2 mutants. These were used to isolate SacII-XhoI ERK2 cDNA fragments which were ligated into the appropriate restriction sites of pET-ERK2 for bacterial expression of (His)$_6$ -tagged recombinant proteins as described above.

C. MEK1

A cDNA encoding a constitutively active mutant of mouse MEK1 (S218D, S222D) [Huang, 1994 #809] with a C-terminal Glu-Tyr-Met-Pro-Met-Glu (SEQ ID NO:15) tag in plasmid pG-MEK1Glu was obtained from Dr. R. L.

Erikson (Harvard University, Cambridge, Mass.). For bacterial expression of N-terminally (His)$_6$-tagged (DD)MEK1, two oligodeoxynucleotides 5'-CATGGCACACCATCACCATCACCATCCCAAG AAGAAGCCGACGCCCATCCAG-3' (SEQ ID NO:16) and 5'-CTGGATGGGCGTCGGCTTCTTCTTGGGATGGTG ATGGTGATGGTGTGC-3' (SEQ ID NO:17), generating an NcoI-PvuII fragment, were annealed and inserted together with a PvuII-BamHI MEK1 cDNA fragment into NcoI-BamHI double-digested pET-BS(+)T7 to yield pET-BS-(His)$_6$-MEK1. BL21(DE3) bacteria were transformed for expression of (His)$_6$-MEK1 as described above for ERK2.

D. JNK3

To clone JNK3, standard techniques well-known by those or ordinary skill in the art were used for manipulations of recombinant DNA.

A BLAST search of the EST database using the published JNK3α1 cDNA [S. Gupta et al., *EMBO J.*, 15, pp. 2760–70 (1996)] as a query identified an EST clone (#632588, Research Genetics) that contained the entire coding sequence for human JNK3α1. Polymerase chain reactions (PCR) using pfu polymerase (Strategene) were used to introduce restriction sites into the cDNA for cloning into the pET-15B expression vector at the NcoI and BamHI sites for expression of the protein in *E. coli*. Due to the poor solubility of the expressed full length protein (Met 1-Gln 422; SEQ ID NO:3), an N-terminally truncated protein starting at Ser residue at position 40 (Ser 40), corresponding to Ser 2 of JNK 1 and 2 proteins (SEQ ID NOS: 33 and 32), preceded by Met (initiation) and Gly residues, was produced. The Gly residue was added in order to introduce an NcoI site for cloning into the expression vector. Further, serial C-terminal truncations were performed by PCR. This construct, which was prepared by PCR using deoxyoligonucleotides 5' GCTCTAGAGCTCC ATGGGCAGCAAAAGCAAAGTTGACAA 3' (forward primer with initiation codon underlined) (SEQ ID NO:18) and 5'TAGCGGATCC TCATTCTGAATTCATTACTTCCTTGTA 3' (reverse primer with stop codon underlined) (SEQ ID NO:19) as primers and confirmed by DNA sequencing, encodes amino acid residues Ser40-Glu402 of JNK3α1 (amino acid 40-402 of SEQ ID NO:3), preceded by Met and Gly residues (herein referred to as "tJNK3α1").

Site directed mutagenesis of tJNK3α1 in the expression vector pET-15B was carried out using the Stratagene® QuikChange™ site-directed mutagenesis kit. Oligonucleotides were designed and synthesized to create the tJNK3α1 M146A, tJNK3α1 M146T and tJNK3αD150G. The sequence of oligonucleotide pairs used in the mutagenesis were:

1) JNK3 M146A—5' CCA AGA TGT TTA CTT AGT Agc GGA ACT GAT GGA TGC AA 3' (SEQ ID NO:20) and its complement;
2) JNK3 M146T—5' CAA GAT GTT TAC TTA GTA acG GGA CTG ATG GAT GCC AAC 3' (SEQ ID NO:21) and its complement; and
3) JNK3 D150G—5' GTA ATG GAA CTG ATG GgT GCC AAC TTA TGT CAA GTG 3' (SEQ ID NO:22) and its complement.

Mutant bases are present in lower case. For each mutation, the tJNK3α1 pET-15B plasmid was denatured and annealed with the appropriate oligonucleotide pair. PCR reactions were performed using Pfu DNA polymerase to yield nicked circular strands which were digested with Dpn1 to remove the non-mutated parental DNA template. The resulting material was transformed into XL1-Blue. All mutations were verified by nucleotide sequence analysis using an Applied Biosystems 373A DNA Autosequencer.

For bacterial expression, *E. coli* strain BL21 (DE3) (Novagen) was transformed with tJNK3α1, tJNK3α1 M146A, tJNK3α1 M146T or tJNK3α1 D150G. These expression constructs were grown at 30° C. in shaker flasks into log phase (OD600~0.8) in LB supplemented with 100 µg/ml carbenicillin. IPTG was then added to a final concentration of 0.8 mM and the cells were harvested 2 hours later by centrifugation.

EXAMPLE 2

Purification of MEK1(DD), ERK2, ERK2 Mutants, JNK3 and JNK3 Mutants

A. ERK2, ERK2 mutants and MEK1(DD)

Unless otherwise stated all steps were performed at 4° C. *E. coli* cell paste, with expressed kinase, was resuspended in 10 volumes/g lysis buffer (50 mM HEPES, pH 7.8, containing 10% glycerol (v/v), 250 mM NaCl, 5 mM β-ME, 5 mM imidazole, 0.1 mM PMSF, 2 µg/ml pepstatin, 1 µg/ml each of E-64 and leupeptin). Cells were mechanically disrupted using a French press and centrifugation at 35,000×g for 60 min. The supernatant was incubated overnight with 1 ml Talon metal affinity resin (Clontech)/5–10 mg estimated protein. Resin with bound kinase was poured into a 1.5×10 cm column and washed with 20 column volumes of lysis buffer without protease inhibitors, followed by 20 column volumes of wash buffer (50 mM HEPES, pH 7.5, containing 10% glycerol (v/v), 100 mM NaCl, 5 mM β-ME and 10 mM imidazole).

Protein was eluted in 2–3 column volumes with wash buffer adjusted to pH 8.0 and 100 mM imidazole. 10% precast SDS-PAGE gels (Novex) were used to identify fractions containing MEK1(DD), which were concentrated by ultrafiltration (Centriprep-30, Amicon) to 2 ml. Concentrated MEK1(DD) was loaded onto a Superdex-75 (60×1.6 cm, Pharmacia) column equilibrated with 20 mM HEPES, pH 7.5, containing 10% glycerol (v/v), 100 mM NaCl and 2 mM DTT at a flow rate of 1 ml/min. Eluted MEK1(DD) fractions were stored at −70° C.

All ERK2 kinases were affinity purified as described for MEK1(DD), then diluted to <25 mM NaCl with 20 mM HEPES, pH 8.0, containing 10% glycerol (v/v) and 2 mM DTT (buffer A), 0.45 µm filtered, and loaded onto a MonoQ (HR 5/5) anion-exchange column equilibrated in buffer A. After washing with 5% buffer B (buffer A+1M NaCl), the ERK2 proteins were eluted in a 5–20% buffer B gradient developed over 60 min at 0.5 ml/min and fractions containing ERK2 were stored at −70° C. Protein concentrations were determined from the $A_{280}$ using calculated extinction coefficients of 23,600 and 42,000 $M^{-1}$ $cm^{-1}$ for MEK1(DD) and ERK2, respectively.

B. JNK3 and JNK3 Mutants

*E. coli* cell paste containing JNK3 was resuspended in 10 volumes/g lysis buffer (50 mM HEPES, pH 7.2, containing 10% glycerol (v/v), 100 mM NaCl, 2 mM DTT, 0.1 mM PMSF, 2 µg/ml Pepstatin, 1 µg/ml each of E-64 and Leupeptin). Cells were lysed on ice using a microfluidizer and centrifuged at 100,000×g for 30 min at 4° C. The 100,000×g supernatant was diluted 1:5 with Buffer A (20 mM HEPES, pH 7.0, 10% glycerol (v/v), 2 mM DTT) and purified by SP-Sepharose (Pharmacia) cation-exchange chromatography (column dimensions: 2.6×20 cm) at 4° C. The resin was washed with 5 column volumes of Buffer A, followed by 5 column volumes of Buffer A containing 50 mM NaCl. Bound JNK3 was eluted with a 7.5 column volume linear gradient of 50–300 mM NaCl, where JNK3 eluted between 150–200 mM NaCl.

EXAMPLE 3

In Vitro Phosphorylation of ERK2 and JNK3 proteins

ERK2 was diluted to 0.5 mg/ml in 50 mM HEPES, pH 8.0, 10% glycerol, 100 mM NaCl, 2 mM DTT, 20 mM β-glycerophosphate, 10 mM $MgCl_2$. Activation was initiated by addition of 2.5 mM ATP and a 1/25 molar ratio of MEK1(DD) for 1 h at 25° C. Activated ERK2 proteins were diluted to 25 mM NaCl and purified by anion-exchange as described.

The ERK2 mutants are phosphorylated in vitro as efficiently as wild-type enzyme by MEK1.

Five mg of JNK3 was diluted to 0.5 mg/ml in 50 mM HEPES buffer, pH 7.5, containing 100 mM NaCl, 5 mM DTT, 20 mM $MgCl_2$, 1 mM ATP. GST-MKK4(DD) kinase (the upstream mutant form of one of the activating kinases of JNK3) was added at a molar ratio of 1 GST-MKK4:2.5 JNK3. After 30 min at 25° C. the reaction mixture was concentrated 5-fold by ultrafiltration in a Centriprep-30 (Amicon, Beverly, Mass.), then diluted back up to 10 ml and an additional 1 mM ATP added. This procedure was repeated three times to remove ADP and replenish ATP. The final (third) addition of ATP was 5 mM and the mixture incubated overnight at 4° C.

The activated JNK3/GST-MKK4(DD) reaction mixture was exchanged into 50 mM HEPES buffer, pH 7.5, containing 5 mM DTT and 5% glycerol (w/v) by dialysis or ultrafiltration. The reaction mixture was adjusted to 1.1 M potassium phosphate, pH 7.5, and purified by hydrophobic interactions chromatography (at 25° C.) using a Rainin Hydropore column. GST-MKK4 and unactivated JNK3 do not bind under these conditions and when a 1.1 to 0.05M potassium phosphate gradient is developed over 60 min at a flow rate of 1 ml/min, doubly phosphorylated JNK3 is separated from singly phosphorylated JNK.

Activated JNK3 (i.e. doubly phosphorylated) was stored at −70° C. at 0.25–1 mg/ml.

EXAMPLE 4

Kinase Assays

A coupled spectrophotometric assay was used in which ADP generated by ERK2, JNK3 or p38 kinase was converted to ATP by PK with the concomitant production of pyruvate from PEP. LDH reduces pyruvate to lactate with the oxidation of NADH. NADH production was monitored at 340 nm using a microplate reader for 20 min at 30° C. Reactions were in 100 mM HEPES, pH 7.6, 10 mM $MgCl_2$, and started by addition of 100 μM ATP. PK (100 μg/ml), LDH (50 μg/ml), PEP (2 mM) and NADH (140 μM) were added in large excess. Addition of 200 μM KRELVEPLTPS-GEAPNQALLR (SEQ ID NO:23) substrate, corresponding to an EGF receptor peptide [F. A. Gonzalez et al., *J. Biol. Chem.*, 266, pp. 22159–63 (1991)], allowed measurement of kinase activity.

In $K_i$ determinations, E+I was pre-incubated for 15 min at 30° C. prior to assay by addition of ATP. Inhibition constants were determined by fitting kinetic data to the Morrison tight-binding equation [J. F. Morrison et al., *Adv. Enzymol. Relat. Areas Mol. Biol.*, 61, pp. 201–301 (1988)] using KineTic (BioKin, 1992). $^{32}P$ incorporation into ATF2 (0.1 mg/ml) by 7.5 nM kinase was assayed for 10 min at 30° C. in 50 mM HEPES, pH 7, 10 mM $MgCl_2$ and 2 mM DTT, and visualized by autoradiography.

The kinase activity of the ERK2 mutants are comparable to wild-type enzyme. However, ERK2(Q105T) shows a 640 to 2,500-fold increased binding affinity for the pyridinyl-imidazoles tested (Table I), using a lower limit of 20 μM for wild-type ERK2 inhibition. ERK2(Q105A) is even more sensitive to this compound class, exhibiting 1,800 to 25,000-fold increased binding (Table I). Mutation of residues, I103L, D106H, E109G, T110A, in addition to Q105T produced an enzyme (herein referred to as "ERK2(5×)") most sensitive to the pyridinyl-imidazoles, ranging from 0.76 nM for SB203580 to 0.4 nM for SB202190. The $K_i$ values correspond to a 2,900 to 50,000-fold increase in potency of binding of these compounds. These results indicate that the larger glutamine side chain at residue 105 accounts for the resistance of ERK2 to pyridinyl-imidazoles.

TABLE 1

$K_M$ for ATP-binding and $K_i$ for pyridinyl-imidazole inhibition of ERK2, ERK2 mutants and p38 kinase.

| Enzyme | $K_M$ for ATP (μM) | Inhibition constants, Ki (nM) | |
|---|---|---|---|
| | | SB203580 | SB202190 |
| ERK2(wild-type) | 76 ± 14 | nil | nil |
| ERK2(Q105A) | 51 ± 6 | 1.2 ± 0.3 | 0.81 ± 0.19 |
| ERK2(Q105T) | 33 ± 4 | 13.0 ± 3.6 | 6.8 ± 0.6 |
| ERK2(5X) | 26 ± 2 | 0.76 ± 0.14 | 0.4 ± 0.04 |
| p38 | 260 ± 30 | 100 ± 30 | 30 ± 8 |

[1]nil indicates no inhibition at 20 μM

Due to the different $K_m$ values for the wild-type and mutant JNK3 enzymes we assayed each one with different ATP concentrations:

| | |
|---|---|
| JNK3 (wild-type) | ATP = 30 μM |
| JNK3 (M105A) | ATP = 150 μM |
| JNK3 (M105A/D109G) | ATP = 600 μM |

Enzyme concentrations in the assay were 5–10 nM. As for ERK2, the kinase phosphate acceptor substrate was the EGF receptor peptide (SEQ ID NO:23) used at 200 μM. Data analysis to determine $K_i$ values was also as described for ERK2.

Wild-type JNK3 differs from ERK2 in that it is moderately sensitive to SB202190. As seen for ERK2, removal of the side-chain of Met146 in JNK3 (the equivalent to Q105 in ERK2) causes a dramatic increase in sensitivity towards SB202190 (~4,000-fold for the M146A mutant). The double mutant is considerably more sensitive than wild-type, but significantly less than observed for the single mutant. The large increase in $K_m$ for this mutant compared to wild-type suggests that ATP binding is also weaker. However, for other pyridinyl-imidazole compounds tested, the double mutant shows enhanced sensitivity relative to both wild-type and the single mutant enzymes. The results are shown in Table 2, below.

TABLE 2

$K_M$ for ATP-binding and $K_i$ for pyridinyl-imidazole inhibition of JNK3 and JNK3 mutants.

| Enzyme | $K_M$ for ATP (μM) | SB202190 $K_i$ (nM) |
|---|---|---|
| JNK3(wild-type) | 15 | 1000 |
| JNK3(M146A) | 75 | 0.23 |

TABLE 2-continued

K_M for ATP-binding and K_i for pyridinyl-imidazole inhibition of JNK3 and JNK3 mutants.

| Enzyme | K_M for ATP (μM) | SB202190 K_i (nM) |
|---|---|---|
| JNK3 (M146A/D150G) | 311 | 1.5 |

EXAMPLE 5

Crystallization and Structure Determination of the ERK2(5x)/SB203580 Complex Crystals of unphosphorylated ERK2(5x) were grown by vapor diffusion when protein (14 mg/ml in 20 mM Tris, pH 7.0, 5 mM DTT, 200 mM NaCl) was mixed with reservoir (100 mM HEPES, pH 7.2, 28–30% (v/v) PEGMME2000, 200 mM (NH_4)_2SO_4, 20 mM β-ME) at a equal volume ratio of protein solution to reservoir and allowed to stand at room temperature. Prior to X-ray data collection at −169° C., a single crystal was equilibrated for 48 h in 100 mM HEPES pH 7.0, 200 mM (NH_4)_2SO_4, 28% PEGMME2000, 5% glycerol, 2% DMSO, and 1 mM SB203580.

X-ray data were collected on an Raxis IIC image plate and processed and scaled using DENZO and SCALEPACK [Z. Otwinowski et al., *Meth. Enzymol.*, 276, pp. 307–326 (1996)]. The crystals had space group symmetry P21, with unit cell dimensions a↑48.6 Å, b↑69.7 Å, c↑60.3 Å and b↑109.25. R-merge for the data was 3.2%, with I/sig(I)↑8.9 at 1.95 Å resolution. The X-ray data comprised 26,737 unique reflections with |F|>σ(F) derived from 69,783 intensity measurements. The data were 96.7% complete overall and 83.2% complete in the 2.01–1.95 Å resolution shell.

X-ray coordinates of unphosphorylated ERK2 were used to construct a model for the refinement of the inhibited ERK2(5x) complex. All thermal factors were set to 20.0 Å². The R-factor after the rigid body and positional refinement was 30% for 10–2.4 Å data. The resolution of the maps and model was gradually increased to 2.0 Å resolution by cycles of model building, positional refinement, and thermal factor refinement, interspersed with torsional dynamics runs. XPLOR was used for model refinement [A. T. Brunger, XPLOR: A system for X-ray crystallography & NMR, Ed., Yale University Press, New Haven, Conn. (Version 3.1) (1992)]. Our current ERK2(5x) model in complex with SB203580 contains 334 protein residues, 283 water molecules, one sulfate molecule, and one inhibitor molecule, and has an R-factor of 21.3% (R-free=28.6%) versus all data with |F|>σ(F) between 6–2.0 Å resolution (23,621 reflections).

PROCHECK and XPLOR was used to analyze the model stereochemistry. Ninety percent of the ERK2 residues were located in the most favored region of the phi-psi plot, and 11% in the additional allowed regions. Deviations from ideal bond lengths and angles were 0.009 Å and 1.5° respectively, and other indications of stereochemistry were average or better then average for a structure determined at 2.0 Å resolution. No electron density was observed for ERK2(5x) amino acids 1–13, 31–33, and 328–335, so these residues were not included in the model.

The crystal structure revealed the interactions that lead to potent binding of the pyridinyl-imidazole compound, SB203580, with residues in the ATP site of ERK2(5x). The para-fluorophenyl ring of SB203580 was shielded from solvent and was within favorable van der Waals distance (<4.5 Å) of the carbon atoms of eight ERK2 side chains; V37, A50, K52, I82, I84, L101, and T105. Comparing this structure with that of wild-type ERK2/ATP, showed that the larger glutamine side chain at position 105 in the wild-type protein would prohibit binding of SB203580 by blocking access to the pocket filled by the para-fluorophenyl ring.

TABLE 3

Other MAP kinases for inhibitor design

| MAP Kinase | SEQ ID NO | Key Amino Acid |
|---|---|---|
| ERK6 | 24 | methionine 109 |
| ERK1 | 25 | glutamine 122 |
| p38-γ | 26 | methionine 107 |
| p38-δ | 27 | methionine 107 |
| JNK3-α2 | 28 | methionine 146 |
| JNK2-α1 | 29 | methionine 108 |
| JNK2-β1 | 30 | methionine 108 |
| JNK2-β2 | 31 | methionine 108 |
| JNK2 | 32 | methionine 108 |
| JNK1 | 33 | methionine 108 |
| JNK1-α2 | 34 | methionine 108 |
| JNK1-β1 | 35 | methionine 108 |
| JNK1-β2 | 36 | methionine 108 |
| p38-β | 37 | threonine 106 |

While we have hereinbefore presented a number of embodiments of this invention, it is apparent that our basic construction can be altered to provide other embodiments of this invention. Therefore, it will be appreciated that the scope of this invention is to be defined by the claims appended hereto rather than the specific embodiments which have been presented hereinbefore by way of example.

Additional contacts were made between the pyridine ring and V39, A52, I84, L106, M108, and L156, while the 4-substituted phenyl ring of SB203580 contacted only L156 and C166. The interactions of the methanesulfonyl group were more extensive, and this group was nearby to D167, N154, S153, and K151. The imidazole ring contacted V39, K54, L156 and C166, and appeared to assist in binding by positioning the three substituents.

Despite the high binding affinity, only one hydrogen bond was made between SB203580 and ERK2(5x).

EXAMPLE 6

Identification of the Amino Acid of Other MAP Kinases to Alter for Binding to Pyridinyl-Imidazole Compounds The amino acid sequence of many other MAP kinases have been published. We have analyzed these sequences by protein alignment means and have determined the amino acid residue that aligns with threonine 106 of p38. If this amino acid is significantly different in character to threonine, then, by changing that amino acid to one with a small side chain (e.g., alanine or threonine), a mutant kinase can be created which can theoretically bind to a pyridinyl-imidazole inhibitor of p38. That complex can then be subjected to molecular modeling means which would allow for the design of an inhibitor of the corresponding native MAP kinase according to the methods of this invention.

This analysis is shown in the table below:

---

We claim:

1. A method for designing an inhibitor of a second serine/threonine protein kinase or a second tyrosine protein kinase comprising the steps of:

(a) providing a first serine/threonine protein kinase or first tyrosine protein kinase having a known three-dimensional structure;

(b) identifying amino acids in an ATP binding site of said first serine/threonine protein kinase or said first tyrosine protein kinase that forms close contacts with a compound know to bind to said ATP binding site;

(c) employing protein alignment means to identify in a second serine/threonine protein kinase or a second tyrosine kinase one or more amino acids that align with, but differ in identity from, said close contact amino acids in said first serine/threonine protein kinase or said first tyrosine protein kinase;

(d) altering an amino acid in the ATP binding site of said second serine/threonine protein kinase or said second tyrosine protein kinase identified in step (c) to produce a mutant second serine/threonine protein kinase or a mutant second tyrosine protein kinase;

(e) determining that said compound binds with at least 10-fold greater affinity to said mutant second serine/threonine protein kinase or said mutant second tyrosine protein kinase than to said second serine/threonine protein kinase or said second tyrosine protein kinase, and (f) using molecular modeling means to determine how to modify said compound to design an inhibitor of said second serine/threonine protein kinase or said second tyrosine protein kinase, wherein said inhibitor binds to said second serine/threonine protein kinase or said second tyrosine kinase with at least 10-fold greater affinity than said compound binds to said second serine/threonine protein kinase or said second tyrosine kinase, respectively.

2. The method according to claim 1, wherein said first serine/threonine protein kinase or tyrosine protein kinase and said second serine/threonine protein kinase or tyrosine protein kinase are both mitogen activating protein (MAP) kinases.

3. The method according to claim 2, wherein said first serine/threonine protein kinase or tyrosine protein kinase is p38 having the amino acid sequence set forth in SEQ ID NO:1.

4. The method according to claim 3, wherein said compound is a pyridinyl-imidazole inhibitor of p38.

5. The method according to claim 4, wherein said compound is selected from SB203580 or SB202190.

6. The method according to claim 2, wherein said second serine/threonine protein kinase or tyrosine protein kinase is selected from:
   a. extracellular-signal regulated kinase 2 (ERK2) having the amino acid sequence set forth in SEQ ID NO:2, wherein amino acid 103 is isoleucine, amino acid 105 is glutamine, amino acid 106 is aspartic acid, amino acid 109 is glutamic acid and amino acid 110 is threonine; or
   b. Jun N-terminal kinase 3 (JNK3, comprising amino acids 40–402 of SEQ ID NO:3, wherein amino acid 146 is methionine and amino acid 150 is aspartic acid.

7. The method according to claim 6, wherein
   a. when said second protein kinase is ERK2, said mutant second protein kinase is an ERK-2 mutant having an amino acid sequence as set forth in SEQ ID NO:2, wherein amino acid 105 is threonine or alanine; or
   b. when said second protein kinase is JNK3, said mutant second protein kinase is a JNK3 mutant comprising amino acids 40–402 of SEQ ID NO:3, wherein amino acid 146 is alanine or threonine.

8. The method to claim 7, wherein in SEQ ID NO:2 amino acid 103 is leucine, amino acid 106 is histidine, amino acid 109 is glycine and amino acid 110 is alanine.

9. The method according to claim 7, wherein in SEQ ID NO:3 amino acid 150 is glycine.

* * * * *